US009940712B2

United States Patent
Henry et al.

(10) Patent No.: US 9,940,712 B2
(45) Date of Patent: Apr. 10, 2018

(54) QUANTITATING DISEASE PROGRESSION FROM THE MRI IMAGES OF MULTIPLE SCLEROSIS PATIENTS

(71) Applicant: THE REGENTS OF THE UNIVERSITY OF CALIFORNIA, Oakland, CA (US)

(72) Inventors: Roland Henry, San Francisco, CA (US); Stephen Hauser, San Francisco, CA (US); Alyssa Zhu, San Francisco, CA (US); Esha Datta, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/304,206

(22) PCT Filed: Apr. 27, 2015

(86) PCT No.: PCT/US2015/027850
§ 371 (c)(1),
(2) Date: Oct. 14, 2016

(87) PCT Pub. No.: WO2015/164882
PCT Pub. Date: Oct. 29, 2015

(65) Prior Publication Data
US 2017/0039708 A1    Feb. 9, 2017

Related U.S. Application Data

(60) Provisional application No. 61/984,640, filed on Apr. 25, 2014.

(51) Int. Cl.
*A61B 5/00* (2006.01)
*G06T 7/00* (2017.01)
*A61B 5/055* (2006.01)

(52) U.S. Cl.
CPC .......... *G06T 7/0012* (2013.01); *A61B 5/0022* (2013.01); *A61B 5/0042* (2013.01);
(Continued)

(58) Field of Classification Search
CPC ..... A61B 5/0042; A61B 5/055; A61B 5/4041; A61B 5/4064; A61B 5/407; A61B 5/4893;
(Continued)

(56) References Cited

U.S. PATENT DOCUMENTS

| | | | | |
|---|---|---|---|---|
| 2012/0197105 | A1* | 8/2012 | Mezer | A61B 5/055 600/410 |
| 2015/0045651 | A1* | 2/2015 | Crainiceanu | A61B 5/055 600/410 |

* cited by examiner

*Primary Examiner* — Siamak Harandi
(74) *Attorney, Agent, or Firm* — Morgan, Lewis & Bockius LLP; Jeffry S. Mann

(57) ABSTRACT

Methods and systems are provided for the automated detection and analysis of structural tissue alterations related to myelin and axons/neurons in one or more biological structures of a patient's nervous system obtained from data from a medical imaging system, or the initial sensing or data collection processes such as, those that could be used to generate an image. In some embodiments, the method comprises, at a system having a memory and one or more processor for processing and displaying images of the biological structure, computationally processing at least a T1 weighted magnetic resonance image of the structure and a T2 weighted magnetic resonance image of the structure in order to analyze at least a portion of the structure of the nervous system using a plurality of stored tissue classifier elements to determine if the portion of the structure correlates with the presence of myelin. Such methods are useful for the detection of diseases associated with demyelination.

14 Claims, 24 Drawing Sheets

(52) U.S. Cl.
CPC .............. *A61B 5/055* (2013.01); *A61B 5/407* (2013.01); *A61B 5/4041* (2013.01); *A61B 5/4064* (2013.01); *A61B 5/4848* (2013.01); *A61B 5/4893* (2013.01); *G06T 2207/30012* (2013.01); *G06T 2207/30016* (2013.01)

(58) Field of Classification Search
CPC . G06T 2207/30012; G06T 2207/30016; G06T 7/0012
See application file for complete search history.

QUANTITATING DISEASE PROGRESSION FROM THE MRI IMAGES OF MULTIPLE SCLEROSIS PATIENTS

CROSS REFERENCES TO RELATED APPLICATIONS

The present application claims priority to U.S. Provisional Application No. 61/984,640 filed Apr. 25, 2014, herein incorporated by reference in its entirety.

BACKGROUND

Multiple sclerosis is a neurodegenerative disease that affects over 2.3 million people around the world. This disease is characterized by inflammatory demyelination, which occurs when the body's immune system attacks the protective myelin sheath that covers the nerves and aids in sending electrical signals. To demonstrate correlations between lesions and clinical symptoms, it is important to be able to characterize the lesions of a patient in a quantitative and objective measure. Many studies use a lesion load metric; however, lesion segmentation is typically a subjective and time-consuming task.

While MRI has been used to identify myelin features in the nervous system, most efforts to characterize myelin involve visual inspection of MRI scans by expert radiologists. This is a time-consuming, expensive, and error-prone process, subject to several subjective biases, not least that humans are notoriously poor at simultaneously assessing statistical relationships between more than two or three variables. A natural tendency is to focus on gross boundaries and local textures. When considering multimodal images, this problem is multiplied several-fold because in order to digest all the available evidence, the analyst has to assess, pixel-by-pixel, the local environment in as many as four distinct modalities. Typically, this forces the analyst to concentrate on only one modality, with the "best" contrast for a particular tissue, and disregard potential contrary evidence in the other modalities. Classification accuracy is subject to variability between researchers and even for the same researcher over time, making a standardized diagnostic test virtually impossible. In most cases, validation of the interpreted image can only be accomplished by histological examination of endarterectomies. Given these importance of myelin detection and analysis to patient health, there is a clear need for improved methods for the detection and analysis of myelin in vivo.

There is weak correlation between lesion volume segmented from T1W and T2W images in diseases like multiple sclerosis. This is in part due to the omission of the degree of injury associated with lesions; i.e. the degree of demyelination or axonal loss. Advanced imaging modalities (including diffusion tensor MRI, magnetization transfer MRI, T1 and T2 relaxation times maps) can provide this information but are technically more challenging to implement and compute and are generally not included in standard imaging protocols. Using the ratio of T2 and T1 scans provides a quantitative metric of demyelination based on the combined T1 and T2 relaxation times without proton density weighting from readily available images in almost all clinical and standard MRI protocols. Furthermore, this ratio diminishes the confounding effects of bias fields on the images.

The ratio of T2 and T1 scans can be used in a novel way as a metric for demyelination in the central nervous system (brain and spinal cord) and degree of damage from myelin-associated disorders, e.g. Siemerling-Creutzfeldt disease, autoimmune disorders, neurological disorders, traumatic injury, or age-related degeneration. By thresholding these maps, methods presented herein can identify which areas are lesions and create a quantified metric to represent the degree of demyelination in lesioned and non-lesioned tissue. The ratio of T2 and T1 scans also provides a quantitative metric in normal appearing CNS tissue that indicates the degree of demyelination and axonal injury inherent in T1 and T2 relaxation times.

Myeloarchitectural features have been visualized using MRI in humans, including the stria of Gennari in V1 (Clark et al., 1992; Barbier et al., 2002; Walters et al., 2003; Bridge et al., 2005; Clare and Bridge, 2005; Eickhoff et al., 2005b; Walters et al., 2007) and tripartite lamination of area 4 (Kim et al., 2009). Other studies have shown regional differences in T1 or T1w image intensity in cortical grey matter, including differences between association cortices and primary sensory and motor cortices using surface (Fischl et al., 2004; Salat et al., 2009) and volume analyses (Steen et al., 2000). Several studies have directly compared MR images to myelin-stained sections of the same tissue. In marmosets, this approach revealed a strong correlation between T1 and T1w intensities and histologically measured myelin content and enabled accurate delineation of several cortical areas (Bock et al., 2009). In humans, a similar approach demonstrated a myeloarchitectonic difference between areas 4 and 3a in ex vivo T1 slices and myelin stained sections (Geyer et al., 2011). Also, fibers of the perforant path are visible in both T2*-weighted images and in myelin stained sections (Augustinack et al., 2010). The myelin-related MR contrast largely reflects differences in lipids (Koenig, 1991) and free and myelin-bound water (Miot-Noirault et al., 1997) concentration, but is also influenced by iron, particularly in T2*-weighted images. However, myelin and iron are strongly colocalized within cortical grey matter (Fukunaga et al., 2010). Thus, it is reasonable to conclude that MR-based signals across the cortical grey matter largely reflect myelin content both directly and indirectly. Sigalovsky et al. (2006) found an increased R1 signal (the inverse of T1) in the posterior medial Heschl's gyms and suggested that this reflected the high myelin content of primary auditory cortex. Yoshiura et al. (2000) reported that Heschl's gyms, particularly the posterior portion, has a lower T2w intensity than the superior or middle temporal gyri. These studies suggest that the myelin content of a cortical area covaries with both T1w intensity and T2w intensity, but in opposite directions.

SUMMARY

Provided herein are methods and systems for the automated detection and, if desired, analysis of myelin in one or more biological structures of a patient's nervous system obtained from data from a medical imaging system, or the initial sensing or data collection processes such as, but not limited to, those that could be used to generate an image. Such methods are useful, for example, for the detection of myelin lesions in a subject and for the prognosis of diseases associated with such myelin lesions (e.g., multiple sclerosis).

In one aspect, provided herein is a method of classifying myelin components to determine whether a biological structure of the nervous system contains myelin. The method includes, at a system having a memory and one or more processor for processing and displaying images of the biological structure, computationally processing at least a T1 weighted magnetic resonance image of the structure and a T2 weighted magnetic resonance image of the structure in order to analyze at least a portion of the structure of the nervous system using a plurality of stored tissue classifier elements developed using statistical modeling to determine if the portion of the structure correlates with the presence of myelin, in which event the portion of the structure is determined to contain myelin. The computationl processing includes registering the T2 weighted magnetic resonance image with the T1 weighted magnetic resonance image by aligning a voxel in the T2 weighted magnetic resonance image with a corresponding voxel in the T1 weighted magnetic resonance image; and dividing, for each voxel in the registered T2 weighted image, a first intensity value in the registered T2 weighted image by a second intensity value of the corresponding voxel in the T1 weighted magnetic resonance image to generate a map of the biological structure.

In certain embodiments, the method is for the determination of a myelin lesion in the biological structure. In some embodiments, the method is for the prognosis of a disease associated with the myelin lesion. In certain embodiments, the disease is multiple sclerosis.

In certain embodiments, the method is for determination of myelin injury to tissue that is normal appearing on any image. In some embodiments, the method is for assessment of myelin in normal tissue.

In some embodiments, the computation processing further includes scaling the map of the biological structure by a constant value.

In certain embodiments, the plurality of stored tissue classifier elements are developed using reference data by multivariate regression.

In some embodiments, the plurality of stored tissue classifier elements is determined by a process selected from the group consisting of post-operative histological examination, direct tissue inspection, and labeling by one or more experts.

In some embodiments, the biological structure is the brain. In certain embodiments, the biological structure is the spinal cord.

In certain embodiments, the computation processing further includes applying a mask to identify a specific tissue type in the biological structure.

In some embodiments, the computation processing further includes generating a Z-score map by comparing the map of the biological structure to a reference map. In certain embodiments, the reference map is generated from data of biological structures from normal subjects. In some embodiments, the reference map is generated from data of biological structures from subjects having a disease (e.g., a demyelinating disease).

In some embodiments, the specific tissue type is white matter. In another embodiment, the specific tissue type is gray matter.

In some embodiments, the biological structure is of the central nervous system. In some embodiments, the biological structure is of the peripheral nervous system.

In some embodiments, the computation processing further includes applying a mask to suppress noise.

In certain embodiments, the method further includes communicating the results of the computational processing and determination of whether the biological structure contains myelin to a remote address.

In another aspect, provided herein is a method of assessing effectiveness of a therapeutic regimen. In some embodiments, the method comprises a) determining a myelin volume in at least a portion of a biological structure of a patient using the method of any of claims 1-13; b) delivering to the patient a therapeutic regimen comprising administration of a drug expected to stabilize or increase myelin volume over the course of the therapeutic regimen; and c) during and/or at the end of the therapeutic regimen, determining whether the myelin volume has stabilized or been increased, thereby allowing assessment of the effectiveness of the therapeutic regimen.

In some embodiments, the therapeutic regimen is for the treatment of a disease associated with demyelination. In certain embodiments, the disease is multiple sclerosis.

These and other aspects and embodiments of the present invention will become evident upon reference to the following detailed description and attached drawings that represent certain preferred embodiments of the invention, which drawings can be summarized as follows:

BRIEF DESCRIPTION OF THE DRAWINGS

FIG. 3 shows the central sulcus of a single subject in axial section with the anterior bank above the posterior bank. The white matter surface is a green contour and the pial surface is a blue contour. The lines delimit area 6 from area 4 on the anterior bank, area 4 from area 3a in the fundus, area 3a from area 3b in the fundus, and area 3b from area 1 on the posterior bank.

(FIG. 6E, FIG. 6J) has 6, 3a, 1. The white marks are in the same position within each hemisphere, allowing direct comparison of the location of the gradients with respect to each other, the myelin map, and the cortical areas.

FIG. 7A and FIG. 7G are myelin maps, FIG. 7D and FIG. 7J are myelin gradients, FIG. 7B and FIG. 7H are probabilistic cytoarchitectonic maps of areas 3b, 4, and 5m. Area 6 is divided into SMA and pre-SMA by a diffusion tractography based parcellation (Johansen-Berg et al., 2004) and only pre-SMA is shown for clarity. E, K are the sum of the gradients of areas 3b, 3a, 4, and 6. FIG. 7C and FIG. 7I are cortical thickness maps corrected for surface curvature. FIG. 7F and FIG. 7L are thickness gradients. As in FIG. 6, the white marks are in the same positions in each panel.

DETAILED DESCRIPTION

Figure 1:
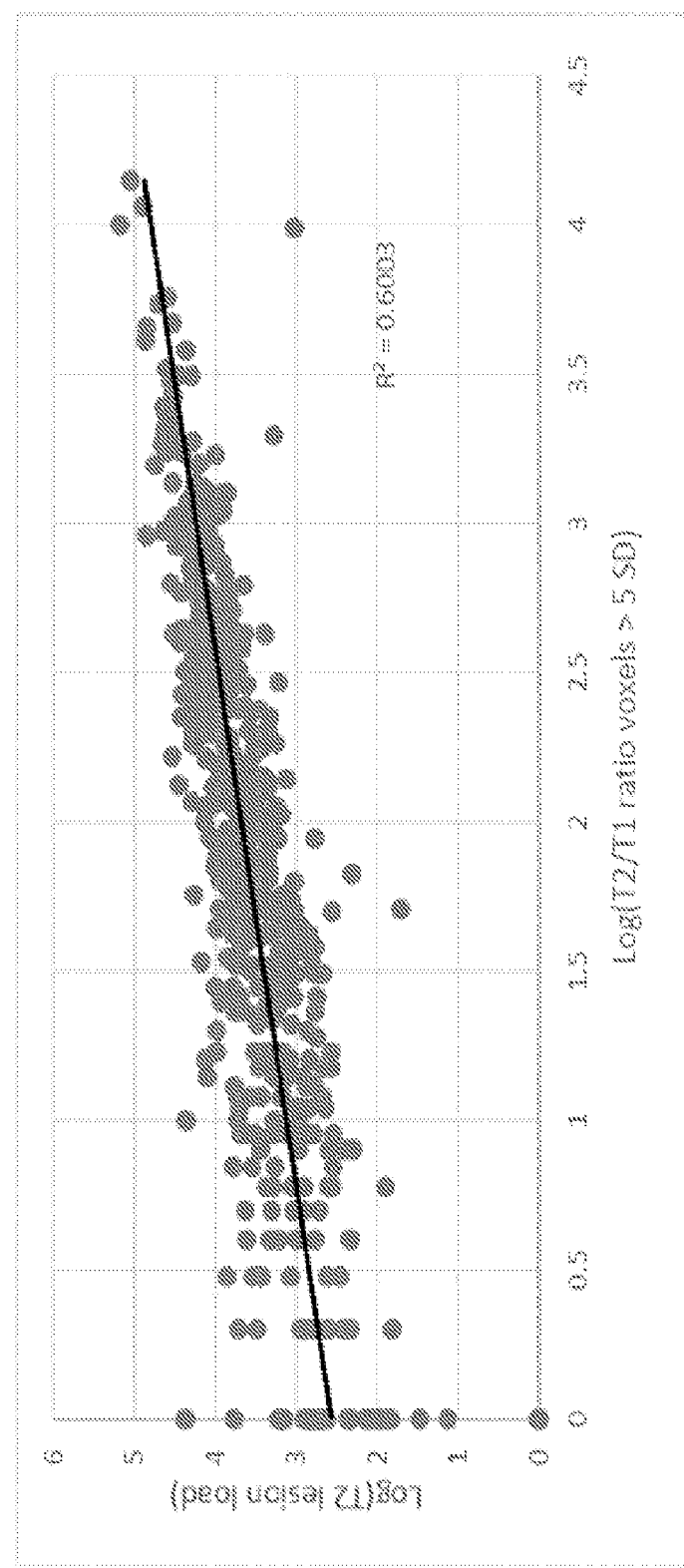
FIG. 1. The log was taken of the normalized T2 lesion load and the voxel count of T2/T1 z-scores with minimum threshold of 5 SD. Plotted against each other, the linear regression (black) yielded a RSQ value of 0.6003.
Figure 2:
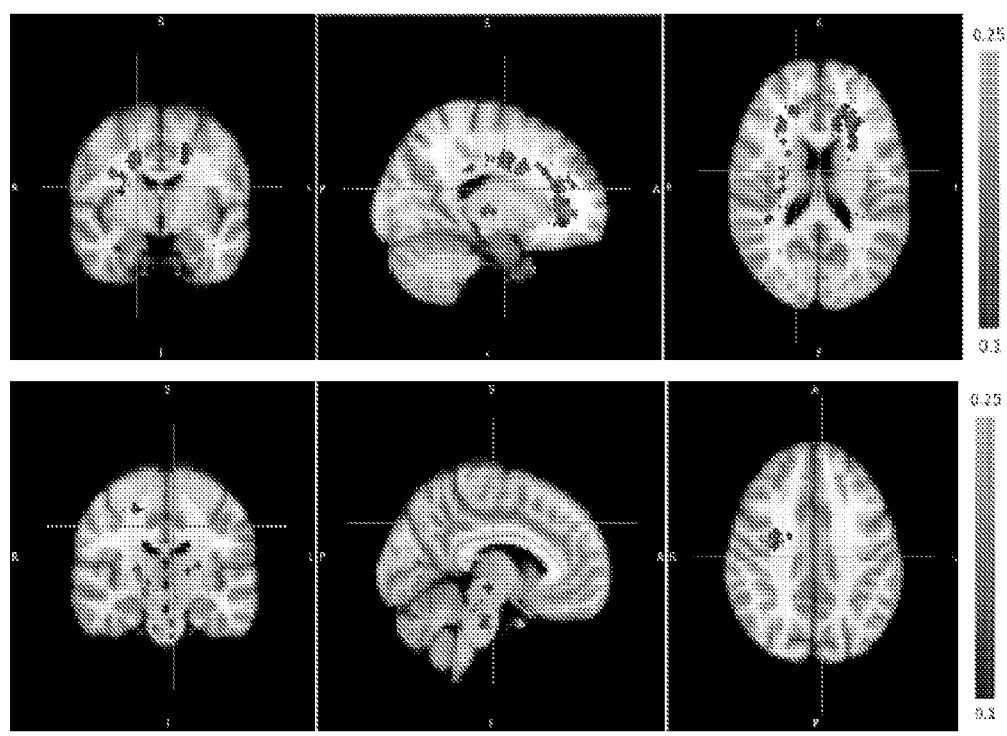
FIG. 2. Correlations are shown in blue, while red is the probabilistic representation of the precentral gyrus ROI from the Harvard-Oxford Cortical Structural Atlas. (A) Analysis of T2/T1 z-score and EDSS score show diffuse frontal white matter correlations, primarily located around the ventricles. (B) voxel-wise analysis between T2/T1 z-score and clinical brainstem scores shows correlated clusters in both brainstem and the motor pathway.

In order for the present disclosure to be more readily understood, certain terms and phrases are defined below as well as throughout the specification.

Definitions

All references cited herein are incorporated by reference in their entirety as though fully set forth. Unless defined otherwise, technical and scientific terms used herein have the same meaning as commonly understood by one of ordinary skill in the art to which this invention belongs. As appropriate, procedures involving the use of commercially available software and hardware are generally carried out in accordance with the manufacturer defined protocols and/or parameters unless otherwise noted.

As used herein, "T2 lesion" and "T2w lesion" refer to hyperintense lesions that they appear as bright spots on the MRI image. The T2-weighted scan is part of conventional MRI technology that is used to monitor and diagnose multiple sclerosis (MS), usually in conjunction with a T1-weighted scan and with or without gadolinium enhancement.

As used herein, "T1 lesion" and/or "T1w lesion" and "black holes" all refer to hypointense lision that are areas of myelin and or axonal damage. These are called hypointense lesions, meaning that they display as dark areas on the MRI image. T1-weighted lesions can also be areas of edema (swelling), which are not permanent and disappear on subsequent scans. The T1-weighted scan is part of conventional MRI technology, which is used to monitor and diagnose multiple sclerosis (MS), usually in conjunction with a T2-weighted scan.

The term "EDSS" as used herein, refers to the Kurtzke Expanded Disability Status Scale (EDSS). The EDSS is a method of quantifying disability in multiple sclerosis. Kurtzke defines functional systems as follows: pyramidal, cerebellar, brainstem, sensory, bowel, bladder, visual, and cerebral.

The term "DTI" and "diffusion tensor imaging," as used herein, refers to a magnetic resonance imaing technique that enables the measurement of the restricted diffusion of water in tissue in order to produce neural tract images instead of using this data solely for the purpose of assigning contrast or colors to pixels in a cross sectional image. It allows the mapping of the diffusion process of molecules, mainly water, in biological tissues, in vivo and non-invasively. Molecular diffusion in tissues is not free, but reflects interactions with many obstacles, such as macromolecules, fibers, and membranes. Water molecule diffusion patterns can therefore reveal microscopic details about tissue architecture, either normal or in a diseased state.

As used herein, "MR relaxation times" in magnetic resonance imaging (MRI) describes how signals change with time. In general, signals deteriorate with time, becoming weaker and broader. The deterioration reflects the fact that the NMR signal, which results from nuclear magnetization, arises from the over-population of an excited state. Relaxation is the conversion of this non-equilibrium population to a normal population. In other words, relaxation describes how quickly spins "forget" the direction in which they are oriented. The rates of this spin relaxation can be measured in both spectroscopy and imaging applications. "T1 relaxation time" is a measure of how quickly the net magnetisation vector (NMV) recovers to its ground state in the direction of $B_0$. T1 relaxation time is also referred to as "spin-lattice relaxation time." "T2 relaxation time" or "spin spin relaxation" refers to the progressive dephasing of spinning dipoles following the 90° pulse as seen in a spin-echo sequence due to tissue-particular characteristics, primarily those that affect the rate of moment of protons, most of which are found in water molecules.

The term "T2/Flair sequences" refers to images that show the total amount of scar from MS from its onset. The pictures show both old and new inflammation. T2/FLAIR lesions can directly account for some symptoms. For example, a brainstem lesion can cause room spinning sensations and balance problems. Cervical (neck) spinal cord T2/FLAIR lesions could cause tingling and numbness in the hands and legs. Many of the lesions may not be causing obvious symptoms. However, continued development of new brain T2/FLAIR lesions could lead to new attacks and thinking problems such as short-term memory loss or trouble keeping track of multiple tasks at the same time. Several treatments can prevent 80% of new T2 lesions from developing in the brain.

The term "z-score" refers to the number of standard deviations an observation or datum is above the mean. Thus, a positive standard score indicates a datum above the mean, while a negative standard score indicates a datum below the mean. It is a dimensionless quantity obtained by subtracting the population mean from an individual raw score and then dividing the difference by the population standard deviation. This conversion process is called standardizing or normalizing.

As used herein, "myelin" refers to the lipid substance forming a sheath (the myelin sheath) around the axons of certain nerve fibers. Myelin is an electrical insulator that serves to speed the conduction of nerve impulses in these nerve fibers, which are called myelinated or medullated fibers. Myelinated nerve fibers occur predominantly in the cranial and spinal nerves and compose the white matter of the brain and spinal cord. Unmyelinated fibers are abundant in the autonomic nervous system. The term "gray matter" refers to areas in the nervous system in which the nerve fibers are unmyelinated. In unmyelinated nerves, impulses are conducted by the propagation of the action potential along the membrane of the axon. In myelinated nerves, impulses are transmitted by an entirely different process, called saltatory conduction, in which the impulse jumps from one node of ranvier to the next. Impulses in myelinated nerves are transmitted hundreds of times faster and require much less energy than in unmyelinated nerves.

As used herein, "voxel-wise multivariate regression" refers to a biological parametric mapping method and is a statistical toolbox for multimodality brain image analysis.

The term "fractional asnisotropy (FA)" refers to a scalar value between zero and one that describes the degree of anisotropy of a diffusion process. A value of zero means that diffusion is isotropic, i.e. it is unrestricted (or equally restricted) in all directions. A value of one means that diffusion occurs only along one axis and is fully restricted along all other directions. FA is a measure often used in diffusion imaging where it is thought to reflect fiber density, axonal diameter, fiber orientation coherence, and myelination in white matter. The FA is an extension of the concept of eccentricity of conic sections in 3 dimensions, normalized to the unit range.

The term "MTR ratio" and "magnetization transfer ratio" both refer to changes in magnetization transfer and is used in neuroradiology to highlight abnormalities in brain stucture. Decreases in MTR indicate that protons bound to the brain tissue matrix have a diminished capacity to exchange magnetization with the free pool of water protons.

The term "QQ plot" refers to a probability plot in statistics that is a graphical method for comparing two probability distributions by plotting their quantiles against each other. First, the set of intervals for the quantiles is chosen. A point (x,y) on the plot corresponds to one of the quantiles of the second distribution (y-coordinate) plotted against the same quantile of the first distribution (x-coordinate). Thus, the line is a parametric curve with the parameter which is the (number of the) interval for the quantile.

Quantitating Disease Progression from MRI Images

The methods provided herein can readily be embodied in software, hardware, or a combination thereof in order to provide automated, non-invasive, and objective detection and analysis (e.g., myelin identification and classification) of multiple sclerosis lesions in a user-friendly and reproducible manner. The subject methods allow researchers, physicians, and patients to readily derive increased benefit from existing disease management and/or treatment strategies.

Multiple sclerosis is a neurodegenerative disease that manifests radiologically in the form of focal white matter lesions and clinically as various forms of physical disability and/or cognitive decline. The standard radiologic metrics used in multiple sclerosis research, such as T2 lesion load, have subpar correlations with measures of disability such as the Expanded Disability Status Scale (EDSS) (Miller, 1998). This has resulted in the development and application of more complex, more informative MRI sequences. Such sequences are time consuming and difficult to introduce into regular clinical practice (Ramli, 2010). Among these sequences are diffusion tensor imaging (DTI) and magnetization transfer (MT) imaging that produces the MTR metric.

Provided herein is a new metric that encapsulates information from T1 and T2W or T2-FLAIR sequences and does not depend directly on the proton density, but strongly on a tissue's relaxation times. Taking the ratio of the two sequence images eliminates the proton density contribution and serves as a form of bias field correction as put forward by Glasser and Van Essen (2011).

In Equation 1, b represents the estimated bias field, and x the myelin content.

$$\frac{T1w}{T2w} \approx \frac{x*b}{\left(\frac{1}{x}\right)*b} = x^2 \qquad \text{Equation 1}$$

T1 relaxation time has also been associated with myelin. The volume of T1 hypointensities in the white matter, also known as black holes, has been shown to correlate with clinical metrics as well as or even better than the conventionally used T2 lesion volume. Furthermore, previous research has shown that the degree of hypointensity found in black holes also correlates with disability scores. The lack of consistency, however, has prevented T1 relaxation time from becoming a metric. Such T1w/T2w ratio was previously used to map cortical areas. The ratio of T1w to T2w signal intensity was mapped to the cortical surface using a customized algorithm. The ratio substantially improves areal localization by increasing the contrast to noise between heavily and lightly myelinated areas and also by mathematically canceling the MR-related intensity bias field (see examples). These studies demonstrate that myelin-based analysis (myelin maps) reveal part or all of the areal boundaries for dozens of cortical areas in a population-average analysis.

As disclosed herein, a simply acquired T2/T1 z-score map provides a clinically feasible metric that correlates with clinical metrics as well as those from magnetization transfer and diffusion tensor images. Such a map was obtained using T1w and T2w MR images from standard 1 mm isotropic 3T protocols. Such simply acquired T2/T1 z-score map provides a clinically feasible metric that correlates with clinical metrics as well as those from magnetization transfer and diffusion tensor images.

As demonstrated by the data provided herein, T2/T1 ratio and T2/T1 ratio z-score are useful as new metrics that are comparable to T2 lesion load with the additional benefit of superior prediction of clinical disability. These maps provide a myelin-weighted metric within the brain or other parts of the nervous system and correlate with MR relaxation times, magnetization transfer, and diffusion MRI metrics. Maps generated by the systems and methods provided herein are useful as quantitative metrics to characterize tissue changes in disease and health. Such T2/T1 z-score maps generated by the systems and methods described herein find use, for example, for the detection of demyelination in biological structures. Furthermore, these data are reflective of load of disease burden by use of varying thresholds (based either on MRW values or z-scores) to define the levels of tissue change.

In certain embodiments, subject systems and methods are useful for the prognosis of a disease associated with demyelination. In some embodiments, the demyelination is associated with a structure of the central nervous system. In some embodiments, the structure is a brain or spinal cord. Diseases associated with demyelination (i.e., demyelinating diseases) in the central nervous system include, but are not limited to, multiple sclerosis, CNS neuropathies, central pontine myelinolysis, tabes dorsalis, and leukoencephalopathies. Demyelinating diseases of the peripheral nervous system include, but are not limited to, Guillain-Barre syndrome, anti-MAG peripheral neuropathy, Charcot-Marie-Tooth Disease, and progressive inflammatory neuropathy. In certain embodiments, the demyelinating disease is multiple sclerosis.

No single imaging modality is likely to be adequate in identifying the estimated 150-200 cortical areas per hemisphere in humans (D. C. Van Essen, M. F. Glasser, D. L. Dierker, J. Harwell, and T. Coalson, unpublished observations). However, progress may be accelerated by using a multimodal approach involving structural and functional imaging carried out on each individual. The Human Connectome Project (http://humanconnectome.org) will use surface-based methods to analyze structural connectivity, resting-state functional connectivity, task-evoked fMRI, and myelin mapping in each of 1200 normal human subjects. Such multi-modal comparisons would ideally be carried out by an observer independent approach that used gradients in the various modalities to delimit cortical areas and identified areas based on their unique patterns of myelin content, structural and functional connectivity, and task activations. Such an approach would go beyond the results presented here and lead to a more accurate parcellation of the cortex. Cross-modal comparisons of myelin maps with resting state fMRI (Glasser et al., 2011) and the other modalities, coupled with careful study of a rapidly growing body of anatomical and functional information may greatly increase our understanding of how to parcellate the complex cortical mosaic.

T2/T1 z-score maps are non-specific with regards to pathological processes. For example, iron deposition and demyelination, both of which occur in multiple sclerosis, have opposite effects on T2. For studies investigating specific cell processes, diffusion tensor and magnetization transfer metrics may still be useful. Changes in T2 and T1 intensities have previously been studied and have been shown to have potential for continued use in research. In this study, we show that combining the T1 and T2 modalities and using them in a quantitative manner allows for a clinically feasible metric that correlates well with those from magnetization transfer and diffusion tensor images as well as clinical measures.

Moreover, the data used in methods provided herein are routinely acquired in clinical MRI protocol for subjects with neurological imaging, thereby providing the opportunity for retrospective studies. The methods provided herein allow for better tracking and prediction of patients' disease progression than conventional lesgion segmentation methods, which can be subjective and time-consuming.

In certain embodiments, the method is carried out using MRI-based methods. In such embodiments, an MRI instrument is used to generate raw magnetic resonance data from which processable magnetic resonance data are derived. One or more different imaging modalities, implemented by one or more different radio frequency pulse sequence series, can allow different tissues and tissue components to be distinguished upon subsequent analysis. Preferred data types generated by such modalities include T1-weighted data and T2-weighted data.

While performing the methods, it may be desirable to pre-process and/or normalize data. In any event, the processable data are computationally processed to determine whether a given portion of the biological structure contains myelin. In some embodiments, tissue or component type determination is accomplished by comparing different tissue types identified in the data to one or more of statistical classifiers. Such classifiers can be developed using known outcome data (e.g., by post-operative histological examination, direct tissue inspection, or labeling by one or more experts) by any suitable process, including logistic regression, decision trees, non-parametric regression, Fisher discriminant analysis, Bayesian network modeling, and a fuzzy logic system. Components and tissues preferably screened for include, for example, white matter or gray matter in the brain.

In certain embodiments, especially those where data from multiple imaging modalities or imaging instruments is used, the data is converted to a common format. In some embodiments, images are computationally brought into registration, often using a landmark, be it one that represents a physical feature or a computational feature.

In some embodiments, a three-dimensional model of the biological structure over at least a portion of the region bounded by the most distantly spaced cross sections being analyzed can be rendered computationally. A plurality of other analyses or operations may also be performed, including calculation of lesion volume, the location and/or composition of lesion, etc. Depending on the analyses or operations performed, the results of the analysis may be output into one or more output files and/or be transmitted or transferred to a different location in the system for storage. Alternatively, the data may be transmitted to a different location.

In another aspect, provided herein is a method for assessing the effectiveness of a therapeutic regimen or determining a therapeutic regimen. Such methods employ the myelin detection and analysis methods provided herein, in conjunction with delivering or determining a therapeutic regimen, as the case may be, depending on the results of the myelin detection, and preferably classification, analysis.

In some embodiments, the therapeutic regimen comprises administration of a drug expected to stabilize or increase the myelination in a patient over time. If desired, the effect of the therapeutic regimen can be assessed by a follow-up analysis, preferably by performing an additional myelin detection, and preferably classification, analysis according to the invention.

In certain embodiments, the instant method will be useful in delivering approved treatment strategies. The instant method will be useful in developing new strategies to assess clinical efficacy of investigational treatments, including those related to drugs being assessed for myelin-associated disorders, e.g., Siemerling-Creutzfeldt disease, autoimmune disorders, neurological disorders, traumatic injury, or age-related degeneration.

In another aspect, provided hererin is a computer program product that comprises a computer usable medium having computer readable program code embodied therein, wherein the computer readable program code is configured to implement an automated method as described herein on a computer adapted to execute the computer readable program code.

In another other aspect, provided herein are computational system configured to execute such computer readable program code, and a business model for implementing such methods, for example, an ASP and API business model. For example, in an ASP model, the medical imaging system and computer system configured to execute the computer readable program code provided herein are located at different locations. Frequently, the computer system resides in a computational center physically removed from each of a plurality of imaging centers, each of which comprises a medical imaging system capable of generating raw data from which processable data can be derived. In preferred embodiments, at least one of the imaging centers communicates raw data to the computational center via a telecommunications link.

With regard to computer systems, they typically comprise a computer adapted to execute the computer readable program code of the invention, a data storage system in communication with the computer, and optionally operably connected to the computer a communications interface for receiving data to be processed by, or for sending data after processing by, the computer.

EXAMPLES

Example 1: Expression, Proteomics, Imaging, Clinical (EPIC) Study

First, T2/T1 ratio maps were generated for 20 controls from the Expression, Proteomics, Imaging, Clinical (EPIC)

study. By registering these maps to the 2 mm resolution MNI standard, an average control atlas of expected values was created. A T2/T1 ratio map was generated for each of the 521 patients and compared to the reference map, in order to generate a z-score map indicating how different the diseased brain is compared to a normal brain.

In accordance with methods of the present invention, each subject's T2-weighted (T2-FLAIR or T2W) image was registered to its corresponding T1-weighted image. The registered image was then divided by the T1 and scaled by a constant factor, yielding a MRW (MR Relaxometry Weighted) metric. The MRW metric does not depend directly on the proton density but rather on T2 and T1 relaxation times.

In some embodiments, the MRW metric is normalized either via phantom scans of the sequences or knowledge of the scaling factors. If acquisition parameters are not held constant, then pseudonormalization can be done using phantom scans with multiple relaxation times. Normalization is also possible using internal reference to non-changing structures, e.g. landmarks, in the field of view.

Conventional computational processing methods to correct for B1 effects can be employed with the present invention but are not necessary since the use of T2-weighted:T1-weighted ratio minimizes strong B1 effects.

Statistical Maps: After non-linearly registering the T1-weighted images to a template space, the output transforms were used to register the MRW maps from individuals to the common space. In the common space, a voxel-wise multivariate regression was run on the reference subjects' data using (for example age and gender as covariates), resulting in coefficient maps. A voxel-wise difference map is then generated for each subject (cases and reference subjects) by subtraction of the predicted MRW value for that subject (for example based on age and gender from the multivariate regression).

A standard error map is generated by computing the voxel-wise standard deviation of the difference map values across the reference subjects. Z-score maps are created for all cases and reference subjects by dividing their difference map by the standard error map. Reference groups can be healthy controls or other cases and include other variables including any covariate that is not of interest in the cases including age, gender, IQ, blood pressure, etc.

Derived Metrics: In addition to the MRW and MRW z-score maps, volumes defined by set thresholds are also generated to quantify the volume of affected tissue. For example, MS lesions can be identified when the value is above a threshold, and the volume of such lesions quantified. The analyses can be restricted to specific tissue types, for example white matter, by use of masks over those regions. Other metrics include the volumes defined by a set of z-score thresholds (e.g. −10, −5, 0, 5, 10) in the white matter, gray matter, or the entire brain.

Both univariate and multivariate regression methods were used to determine whether this metric has a strong correlation for the existing T2 lesion load measurements as well as measures of clinical symptoms, such as the Expanded Disability Status Scale (EDSS) score. In addition, we used univariate regression methods to compute spearman coefficients for each voxel and generate correlation maps for various clinical measures. The resulting maps were multiplied by a white matter mask, thresholded, and then morphologically opened with a 2 mm Gaussian kernel to eliminate noisy voxels.

Voxel count of white matter z-scores thresholded at 5 and 10 standard deviations (SDs) displayed high correlations to T2 lesion volume with RSQ values of 0.57 and 0.54 respectively. Stepwise multivariate regression including volume above T2/T1 ratio of 5 SDs, T2 lesion volumes, and whole brain volume selected only brain volume and T2/T1 ratio volume to be important in predicting EDSS score, and not T2 lesion volume. Voxel-wise correlation maps with EDSS versus T2/T1 ratio z-score showed notable regionality with higher spearman correlations around the ventricles and frontal white matter while correlations with the clinical brainstem scores indicated clusters in the brainstem and motor pathways.

Example 2: Subjects and Image Acquisition

The methods were developed on a single subject and then applied to two separate datasets obtained with differing imaging parameters. All datasets were acquired using protocols approved by the institutional review boards. The first included 69 control subjects (37 males, 32 females, age mean 22+/−6) from the Conte Center (see Acknowledgements). Subjects were scanned at Washington University in St. Louis and at Northwestern University on Siemens 3T Tim Trios using a 12-channel head coil. A 3D T1w Magnetization Prepared RApid Gradient Echo (MPRAGE: TR=2400 ms, TE=3.16 ms, TI=1000 ms, 8° flip angle, bandwidth=220 Hz/Pixel, echo spacing=7.5 ms, FOV 256 mm×256 mm×176 mm, matrix 256×256×176, 1 mm isotropic resolution) sequence was acquired. A GeneRalized Autocalibrating Partially Parallel Acquisition (GRAPPA) factor of 2 in combination with 50% phase oversampling (acquisition time 8 min) gave an SNR level intermediate to that with no parallel imaging and that with GRAPPA of 2 and no phase oversampling. A 3D T2w Sampling Perfection with Application optimized Contrast using different angle Evolutions (SPACE: TR=3200 ms, TE=449 ms, variable flip angle, bandwidth=698 Hz/Pixel, echo spacing=3.26 ms, Turbo Factor=139, FOV 256 mm×256 mm×176 mm, matrix 256×256×176, 1 mm isotropic resolution) sequence was acquired. A GRAPPA factor of 2 was used with no phase oversampling (acquisition time of 5 min). Both scans were acquired sagittally. The original single subject was scanned with identical parameters to the above.

The second dataset includes the 10 control subjects (all male, mean age=42+/−11) from the publicly available Brain Mutlimodality dataset from NAMIC (see Acknowledgements). The data were acquired on a 3T General Electric (GE) scanner at Brigham and Women's Hospital in Boston using an 8-channel head coil and GE's parallel imaging technology Array Spatial Sensitivity Encoding Techniques (ASSET) was used with a SENSE (SENSitivity Encoding) factor of 2. A T1w SPoiled Gradient Recalled sequence (SPGR: TR=7.4 ms, TE=3 ms, TI=600 ms, 10° flip angle, FOV 256 mm×256 mm, matrix 256×256, 1 mm slices) and a T2w eXtended Echo Train Acquisition (XETA: TR=2500 ms, TE=80 ms, FOV 256 mm×256 mm, matrix 256×256, 1 mm slices) were acquired. Data were downloaded from the NAMIC MIDAS website: http://insight-journal.org/midas/collection/view/190.

Example 3: Surface Generation and Processing of T1w Volumes

The original unresampled T1w volumes were processed through FreeSurfer 4.5's default recon-all pre-processing pipeline (http://surfer.nmr.mgh.harvard.edu/), which includes brain extraction, intensity normalization, segmentation, generation of white and pial surfaces, surface topology correction, inflation of surfaces to a sphere, and spherical registration to the $fs_{average}$ surface based on a measure of surface shape (Dale et al., 1999; Fischl et al., 1999a; Fischl et al., 1999b; Fischl et al., 2002; Sled et al., 2002; Ségonne et al., 2004). The most accurate surfaces were obtained using unresampled T1w volumes, likely through minimization of partial volume effects. FreeSurfer white and pial surfaces were converted to GIFTI format with application of a transformation matrix to correct for a translational offset ('c_ras') so that the surface and volume would line up. Using Caret software (Van Essen et al., 2001) a midthickness surface was generated by averaging the white and pial surface coordinates. The white, pial, and midthickness surfaces with the original number of nodes are referred to as "native" mesh surfaces.

The registered spherical surface (sphere.reg) was converted to GIFTI format and resampled onto the $fs_{average}$ template spherical surface using Caret's 'create deformation map' function. The resultant deformation map between the native mesh surfaces and the $fs_{average}$ surface was applied to bring the native mesh surfaces into register with and on to the 164 k vertex $fs_{average}$ left or right mesh (hereafter fs_L or fs_R). The fs_L and fs_R meshes are not in register, so we used a landmark-based registration between them and a hybrid left and right $fs_{average}$ template (hereafter fs_LR), creating deformation maps for left and right hemispheres (D. C. Van Essen, M. F. Glasser, D. L. Dierker, J. Harwell, and T. Coalson, unpublished observations). We applied these deformation maps to the subjects' fs_L and fs_R resampled surfaces, bringing their left and right hemispheres into register and onto the 164 k vertex fs_LR mesh. These steps enable quantitative comparisons of surface-mapped data across subjects and hemispheres in a vertexwise fashion.

Example 4: Processing of T2w Images and Generation of the T1w/T2w Ratio Image Volume The T2w image was registered to the T1w image using FSL's FLIRT (Jenkinson et al., 2002) with 6 parameters (rigid body) and the mutual information cost function. This registration precisely aligned all brain regions except for small portions of ventral orbitofrontal cortex, overlying the sphenoid sinus, and inferior temporal cortex, overlying the mastoid air cells. In these areas, the gradient echo T1w and spin echo T2w data were affected differently by magnetic susceptibility-induced signal dephasing and signal loss (see artifactual results). The T2w image was resampled using the spline interpolation algorithm of FSL's applywarp tool. Spline interpolation minimizes the white matter and CSF contamination of grey matter voxels that would result from the volumetric blurring inherent in trilinear interpolation. Spline interpolation yielded similar results when applied only to the T2w image or when applied separately to both the T1w and T2w images so that they were resampled the same number of times.

Division of the T1w image by the aligned T2w image mathematically cancels the signal intensity bias related to the sensitivity profile of the radio frequency receiver coils, which is the same in both images. Taking the ratio also increases the contrast related to myelin content. A simple approximation (Eq. 1) explains both effects: if myelin contrast is represented by x in the T1w image and 1/x in the T2w image and the receive bias field is represented by b in both images, the T1w/T2w ratio image equals $x^2$, i.e. enhanced myelin contrast, with no bias field contribution. Because the noise in the T1w and T2w images is uncorrelated, there is increased myelin contrast relative to the noise (i.e., increased CNR).

$$\frac{T1w}{T2w} \approx \frac{x*b}{(1/x)*b} = x^2 \quad (1)$$

Alternative bias field correction methods such as FSL's FAST (Zhang et al., 2002) and MINC's nu_correct (Sled et al., 1998) are not sufficiently accurate for the myelin mapping technique presented here. As demonstrated below, myelin mapping relies on detection of subtle differences in grey matter intensity that are obscured by either incomplete correction of the bias field or by errors in the bias field that can occur around the exterior of the brain. These errors take the form of local inhomogeneities between superficial cortex on the gyral crowns and deeper cortex in the fundi of sulci, and they result from the steep image intensity gradient between brain tissue and extra-cerebral tissues. These errors become more apparent when one runs a bias field correction utility multiple times in an attempt to completely remove the bias field. Intensity variations due to transmit field biases are minimal when using body transmit coils, as used here with the Siemens 3T Trios, because such coils produce very uniform transmit fields over the head. Further, some of the residual biases from the transmit field may also be reduced when dividing the images, since, while the transmit profiles between the two sequences are different; they are correlated. Indeed, there was no discernible global signal bias in our T1w/T2w ratio images, as the low frequency variations in grey and white matter were anti-correlated. We would expect them to be correlated if a bias field were present, as they are in the raw T1w and T2w images. These assumptions will not apply at higher resonant frequencies (i.e., at higher field strengths like 7T) where local transmit coils are used and where the transmit field biases are much stronger (Van de Moortele et al., 2009). In this case, it will be necessary to use sequences for the ratio that have very similar transmit profiles.

Figure 3A:
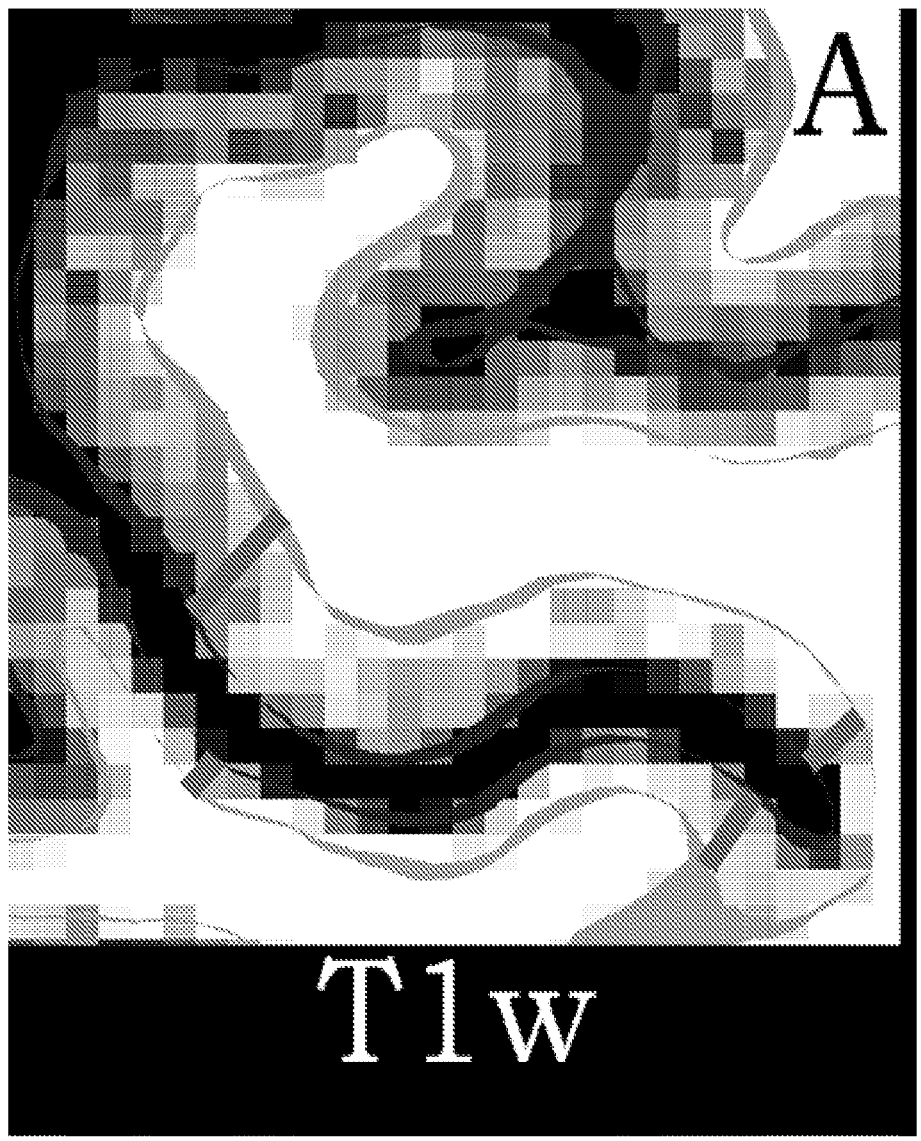
FIG. 3A is a T1w image.
Figure 3B:
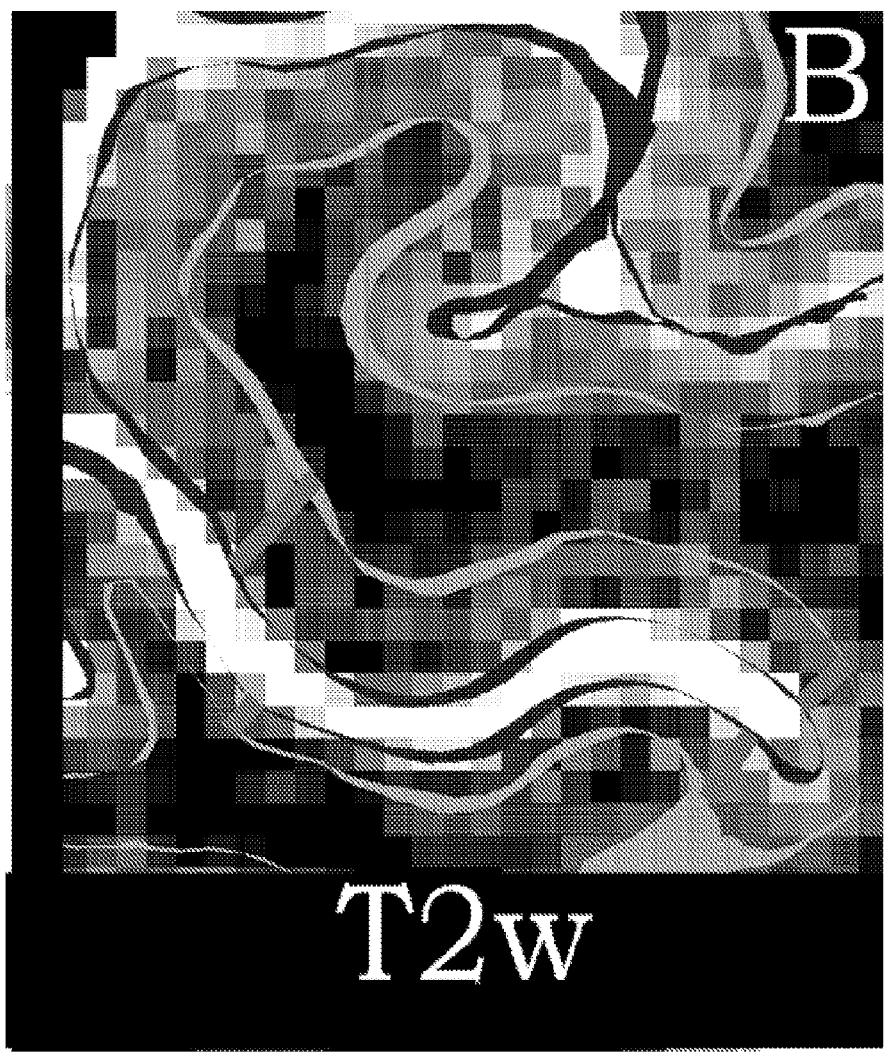
FIG. 3B is a T2w image.
Figure 3C:
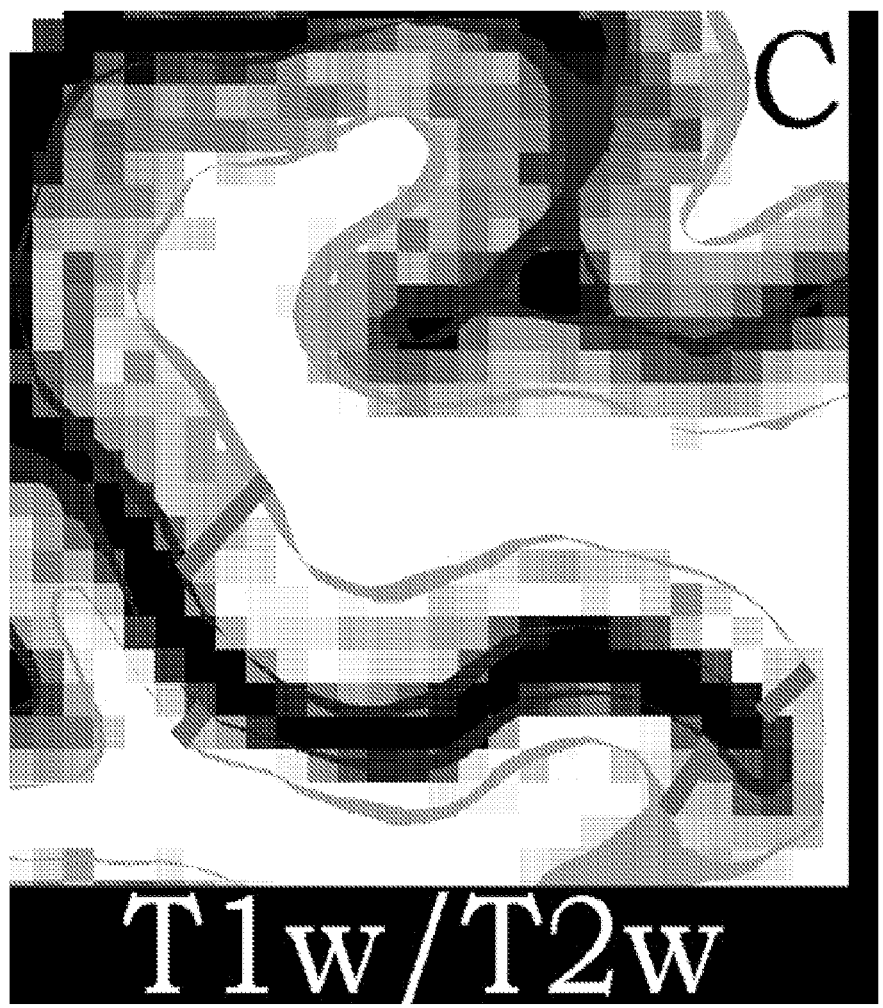
FIG. 3C is the T1w/T2w image in grey scale.
Figure 3D:
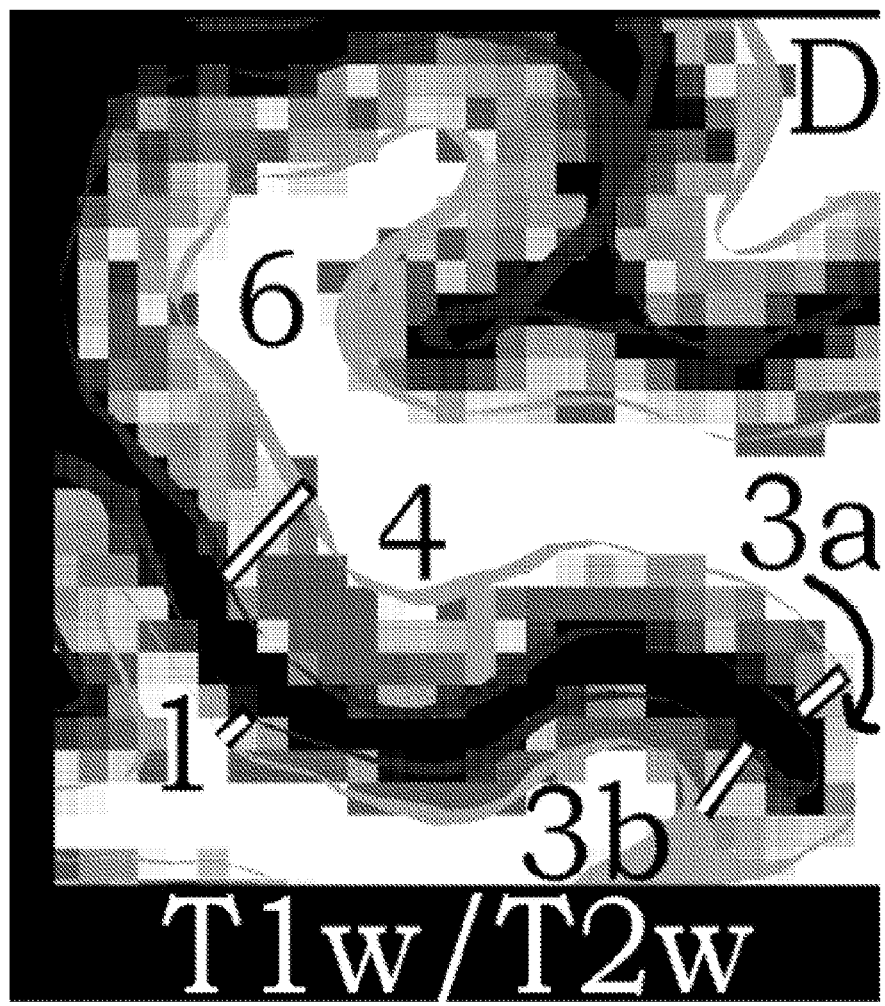
FIG. 3D is the T1w/T2w image in color scale. All volumetric data are unsmoothed. From these images, it is apparent that areas 4 and 3b are more heavily myelinated than areas 6, 3a, and 1. The scale in panel D is T1w/T2w=1% (purple) to 99% (red).
Figure 4A:
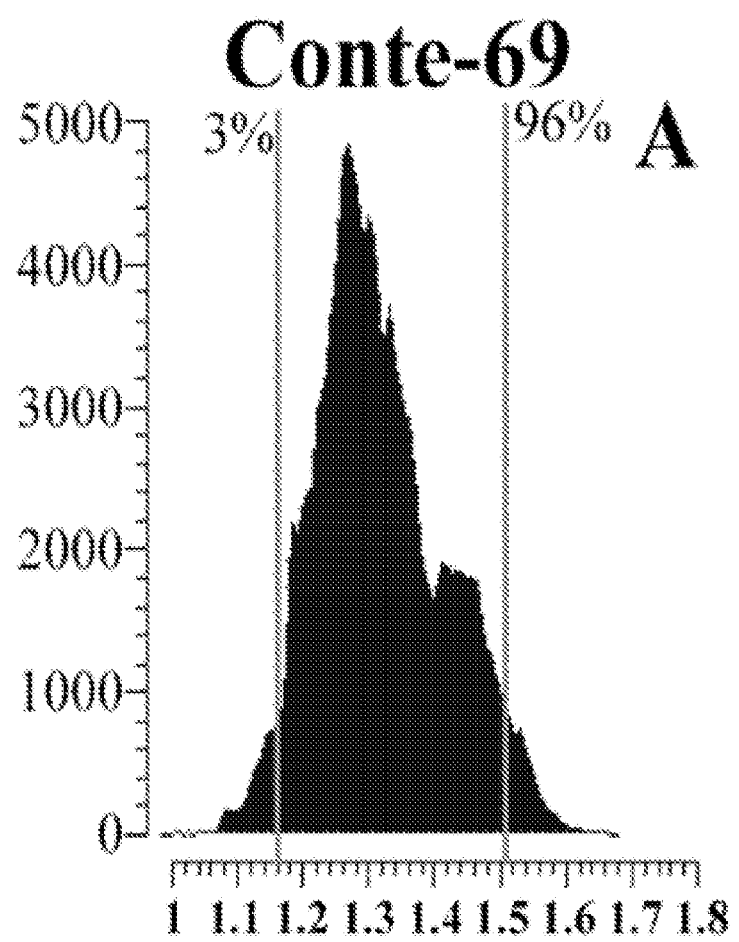
FIG. 4 is a comparison of image histograms from the datasets in FIG. 5. The grey lines mark the minimum (black=3%) and maximum (red=96%) for the color palette used in FIG. 5. The shapes of the T1w/T2w histograms are very similar, but their absolute magnitudes differ markedly. The values for the NAMIC-10 group are twice as high as for the Conte-69 group, reflecting the fact that the data were collected on different scanners using different pulse sequences (see Examples). The top row is the left hemisphere and the bottom row is the right hemisphere.
Figure 4B:
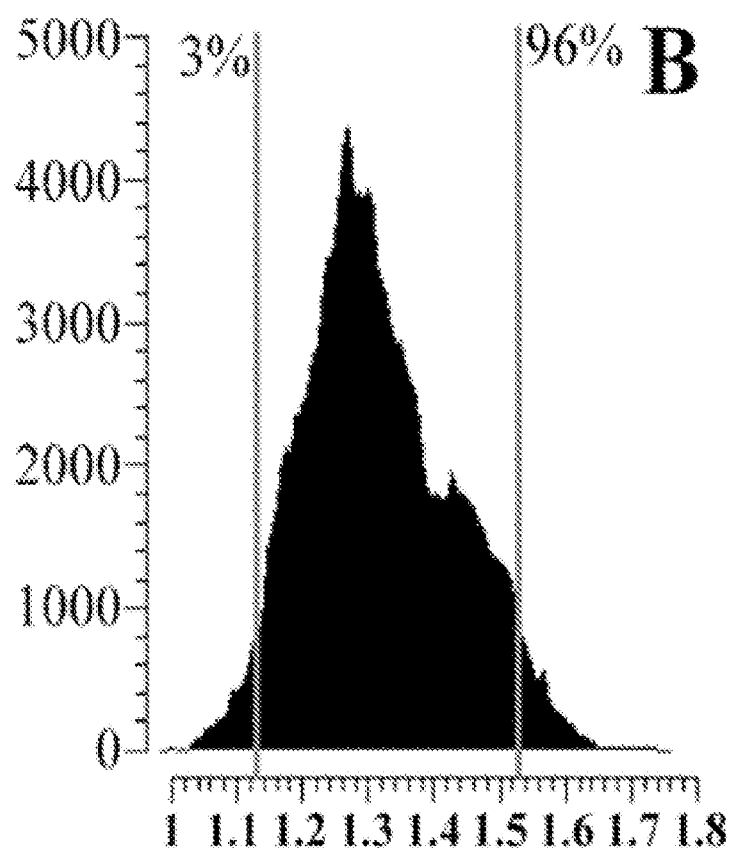
Figure 4C:
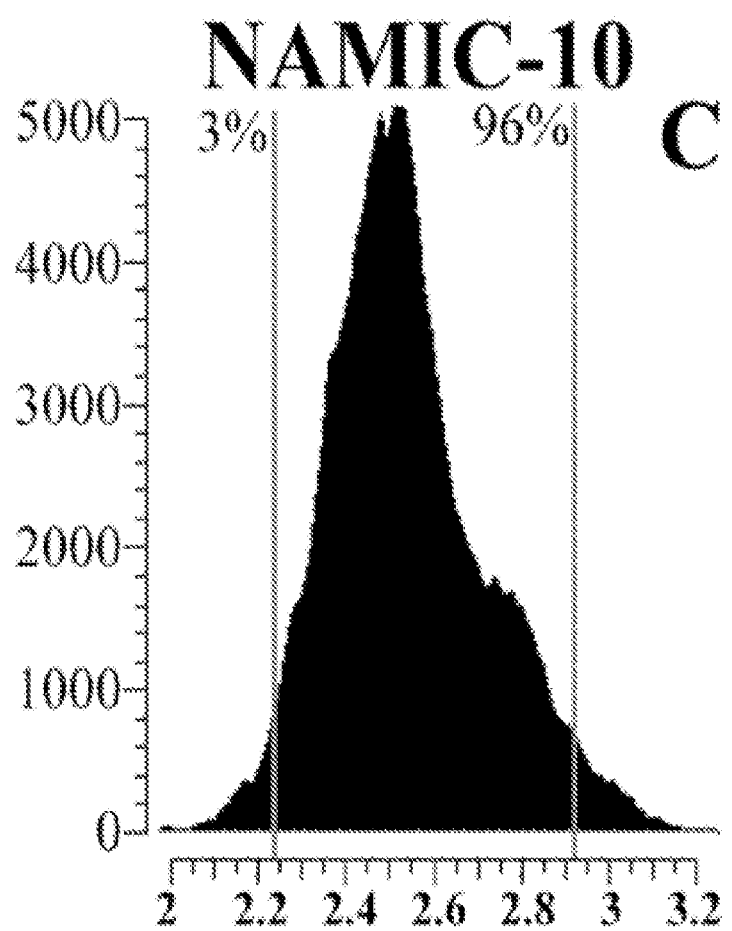
Figure 4D:
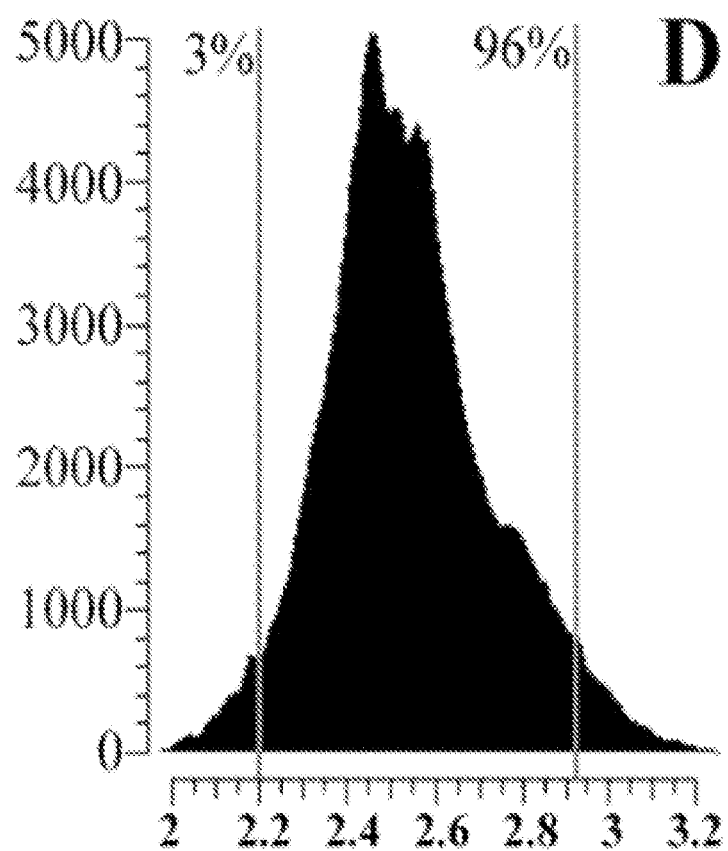
Figure 4E:
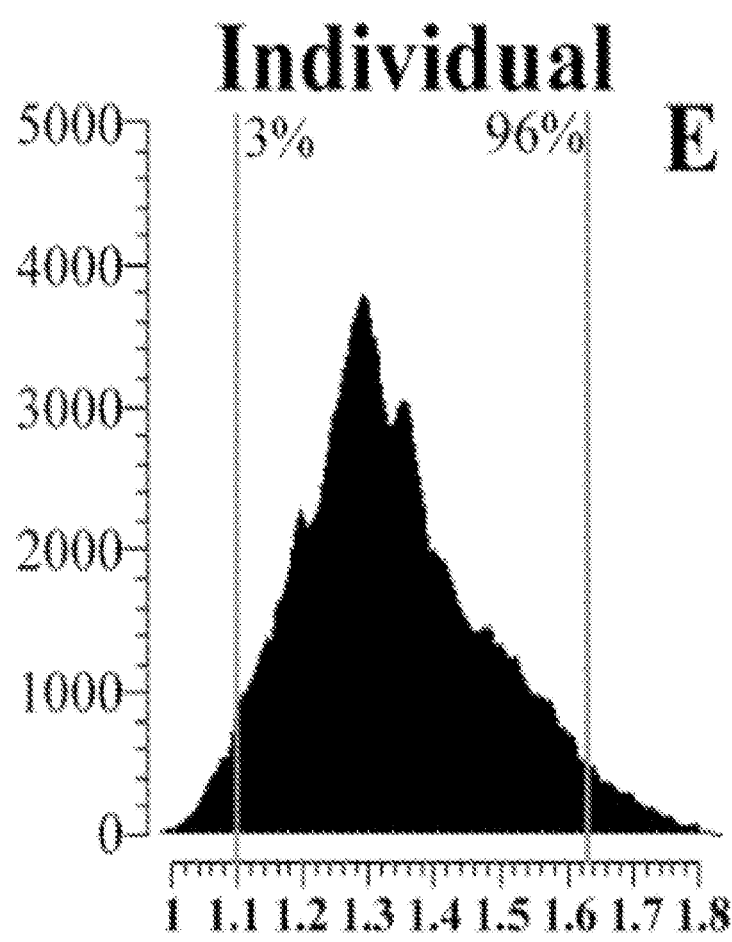
Figure 4F:
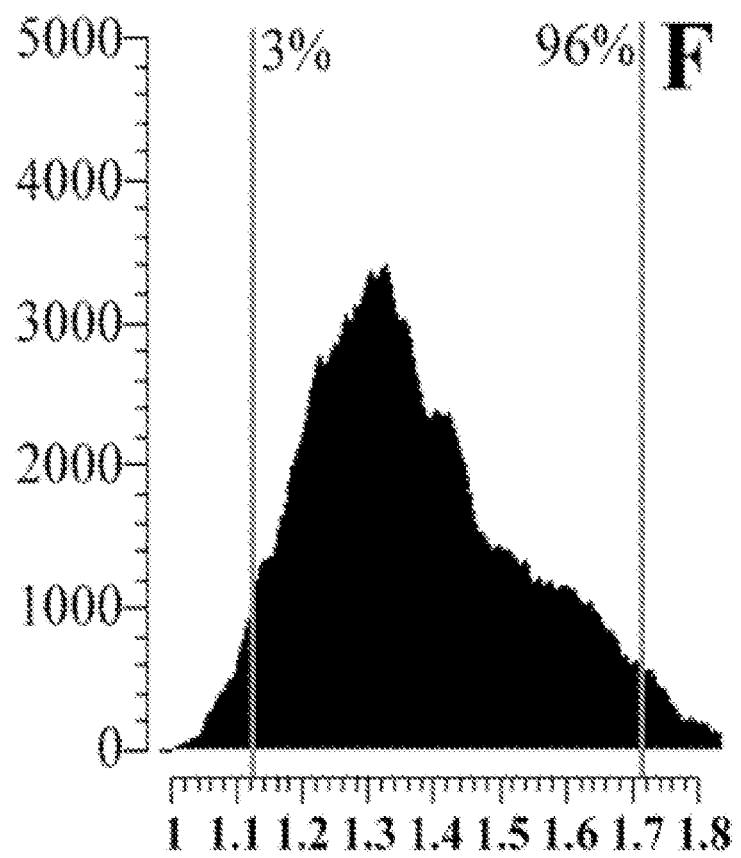
Figure 5:
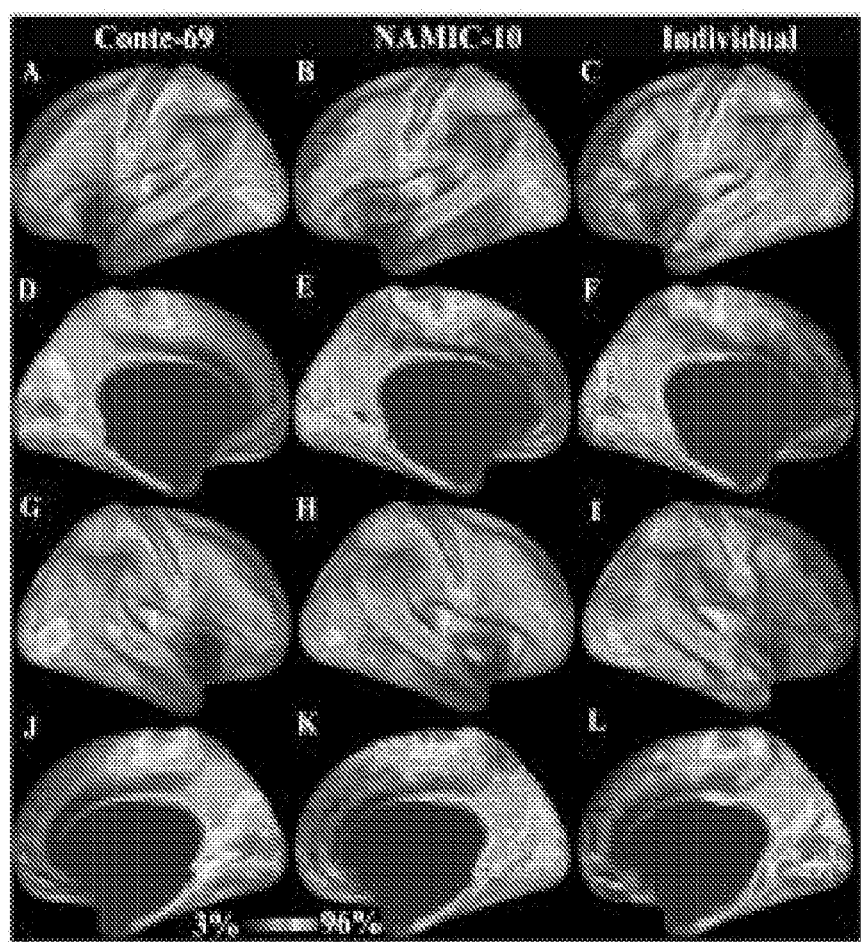
FIG. 5 depicts an overall comparison of the T1w/T2w ratio in two groups and an individual subject on the freesurfer LR inflated surface. Row 1 is the left hemisphere lateral view, row 2 is the left hemisphere medial view, row 3 is the right hemisphere lateral view, and row 4 is the right hemisphere medial view. The left hand column (A,D,G,J) is the Conte-69 average data. The center column (B,E,H,K) is the NAMIC-10 average data. The right hand column (C,F,I,L) is the single subject scanned like the Conte-69. The single subject data have been smoothed with 5 mm FWHM surface geodesic Gaussian smoothing (described in the methods). Note the strong agreement of the patterns across groups and hemispheres. In all medial surface panels, the medial wall is masked.
Figure 6:
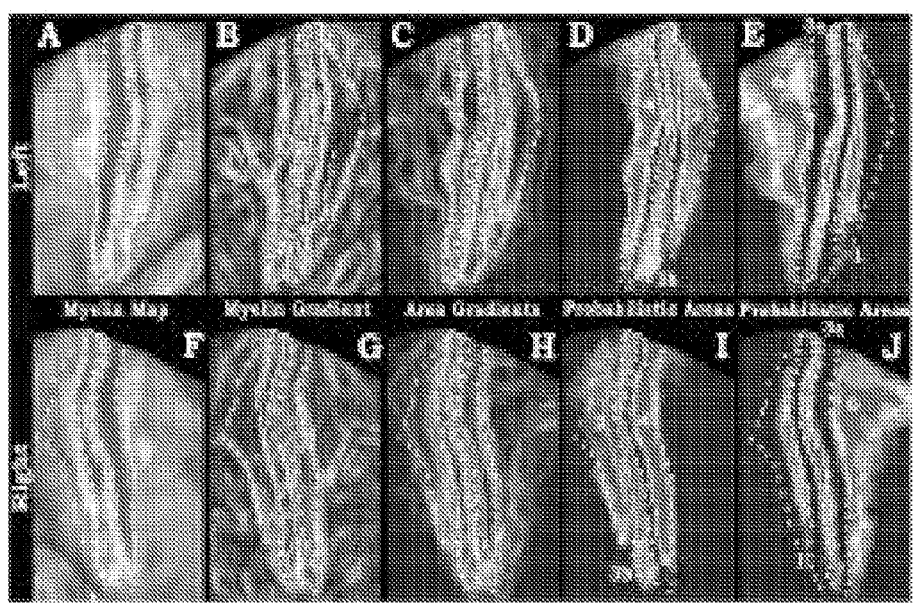
FIG. 6 is a comparison of myelin maps and gradients to probabilistic cytoarchiteconically defined cortical areas and gradients. The top row shows the left hemisphere and the bottom row the right hemisphere in the region of the central sulcus. The first column (FIG. 6A, FIG. 6F) shows myelin maps as in FIG. 5. The second column (FIG. 6B, FIG. 6G) is the gradient of the myelin maps, i.e. regions of rapid intensity changes. The third column (FIG. 6C, FIG. 6H) is the sum of the gradients of the probabilistic cortical areas shown in the last two columns (FIG. 6D, FIG. 6E, FIG. 6I, FIG. 6J). These two columns alternate cortical areas, (FIG. 6D, FIG. 6I) has 4, 3b, 2.
Figure 7:
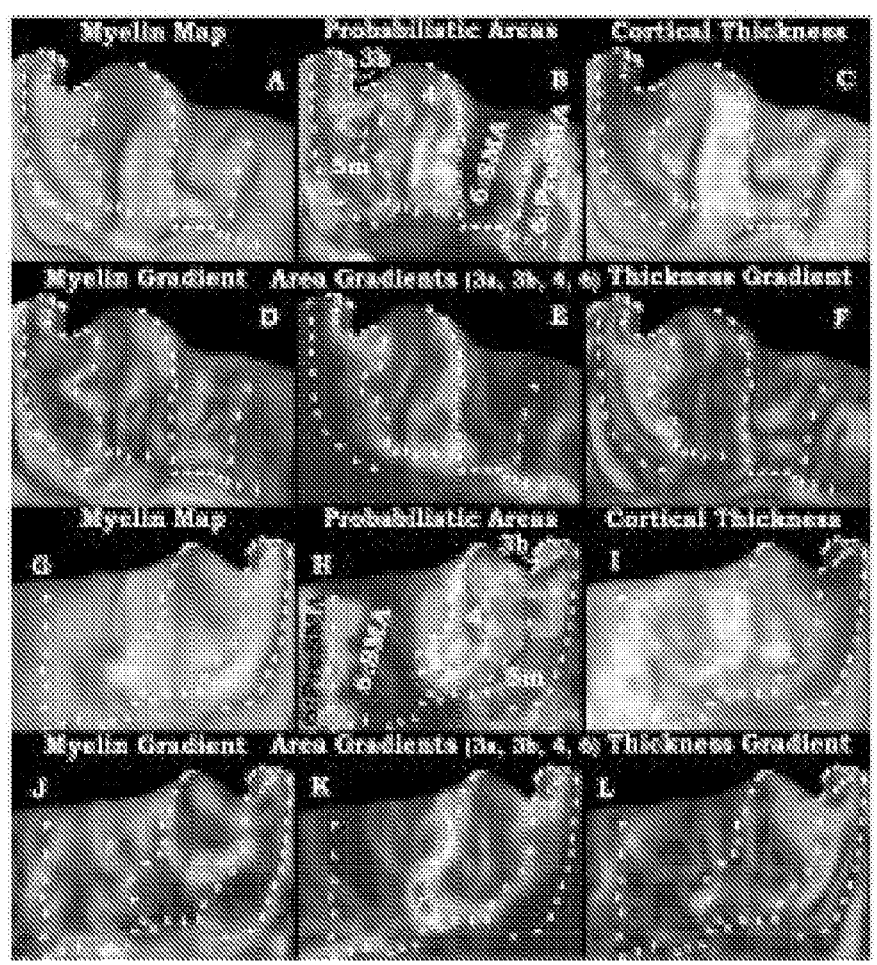
FIG. 7 shows a comparison of myelin maps and their gradients to probabilistic cortical areas and their gradients and also to cortical thickness maps and their gradients. The top two rows show the left paracentral lobule, and the bottom two rows show the right paracentral lobule.
Figure 8:
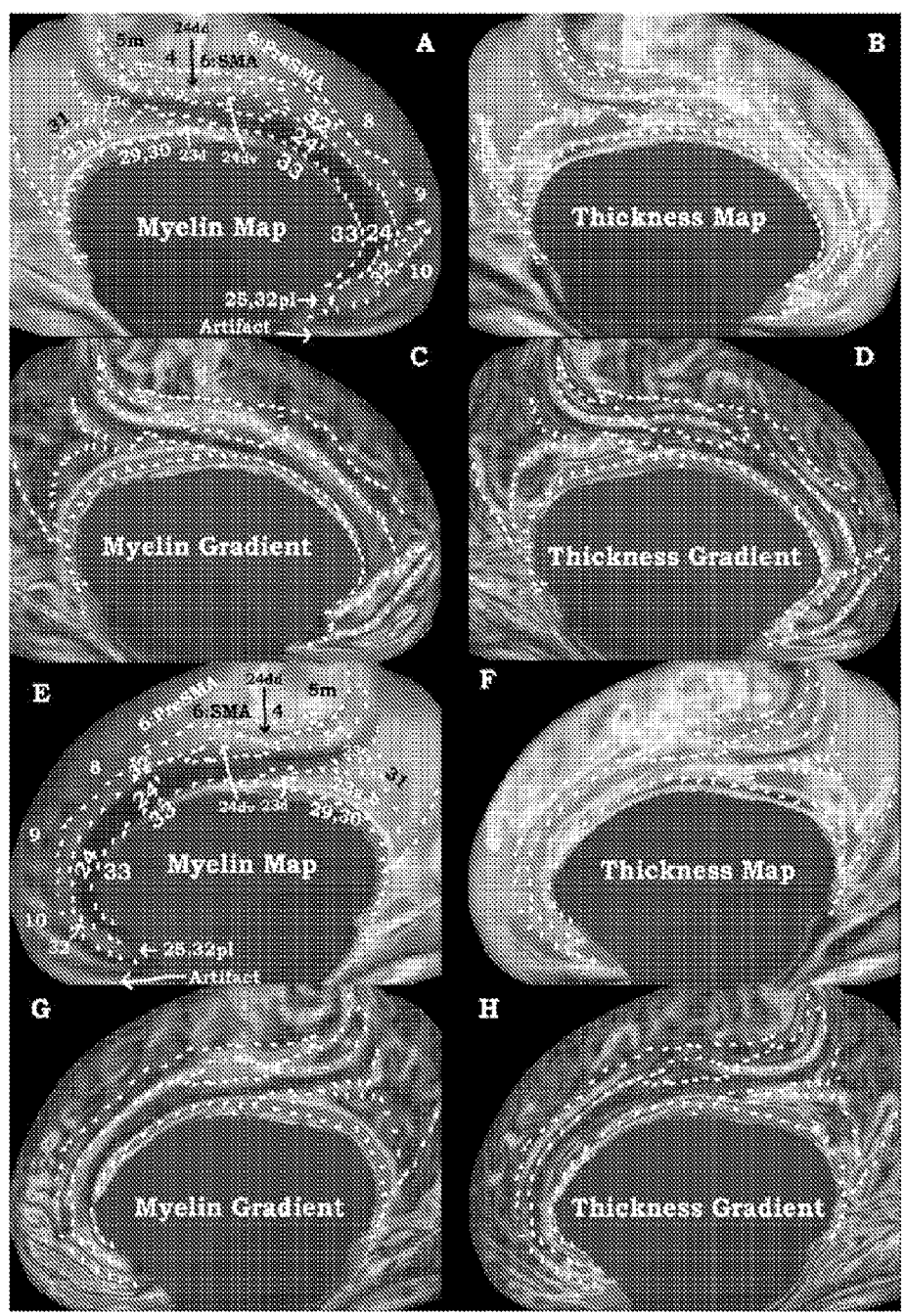
FIG. 8 show myelin and thickness maps and demonstrates that their gradients are used to define putative cortical areas in the cingulate region on an inflated surface. White marks are in the same positions within each hemisphere and were drawn on either the myelin gradients, the thickness gradients, or the inferior borders of probabilistic areas 4 and 6 (data not shown). The top two rows are the left hemisphere and the bottom two rows are the right hemisphere. Panels A and E show the myelin maps, panels B and F show the cortical thickness maps corrected for surface curvature, panels C and G show the myelin gradients, and panels D and H show the thickness gradients.
Figure 9:
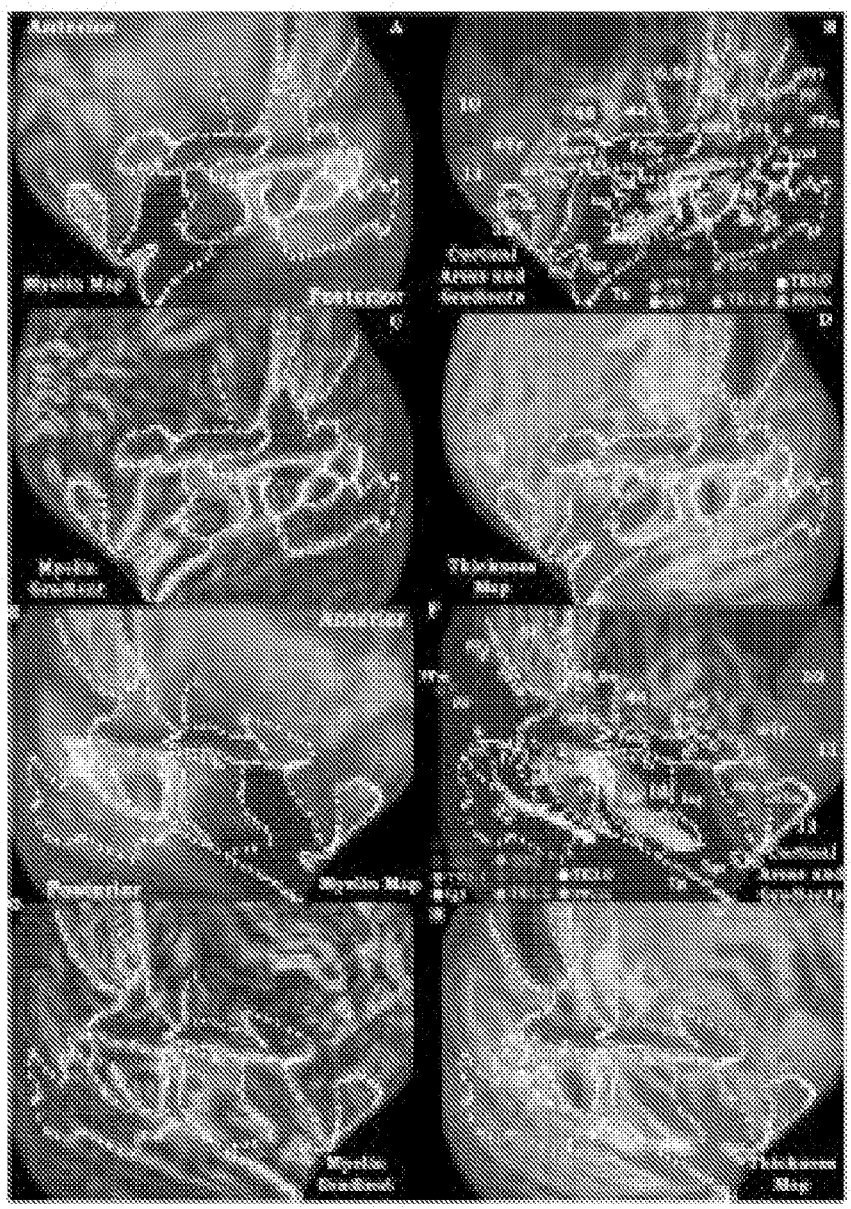
FIG. 9 shows myelin maps, gradients of myelin maps, and thickness maps as compared to cortical areas and gradients of cortical areas in the perisylivan region on an inflated surface. White marks are in the same positions within each hemisphere and were drawn on the myelin gradients and gradients of probabilistic areas. The top two rows are the left hemisphere and the bottom two rows are the right hemisphere. Panels A and E show the myelin maps. Panels B and F include the gradients of the probabilistic areas in FIG. 6 and the gradients of surface mapped areas 44 and 45. The orbito-frontal parcellation was derived from surface mapped architectonic parcels from the 4 hemispheres presented in Ongur et al (2003). The spheres and associated colored patches are 3D centers of gravity of volume mapped cortical areas and a hard segmentation of the volume mapped cortical areas thresholded at 4 subjects from the SPM anatomy toolbox (Eckhoff et al 2005). Panels C and G show the myelin gradients. Panels D and H show the cortical thickness maps corrected for surface curvature. Note that Tga is more lightly myelinated than Tg, but the difference is not visible in panels A and E because both are extremely lightly myelinated compared to the rest of the brain.
Figure 10:
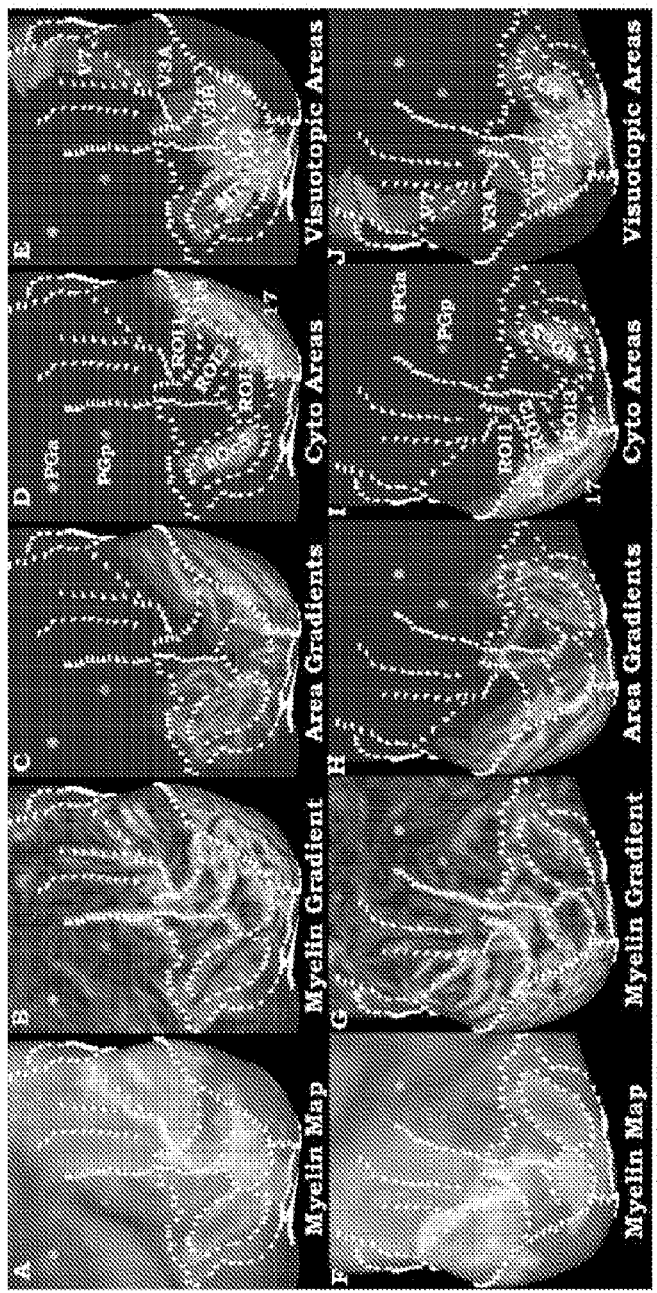
FIG. 10 shows myelin maps, gradients of myelin maps, cytoarchitectonic areas, gradients of cytoarchitectonic areas and visotopic areas of the lateral visual cortex on an inflated surface. Because of increased variability of the gradients within this region, white marks were drawn on a map of left X right myelin gradients, which highlights gradients that are consistent across hemispheres and are in the same positions in all images. For the area 18 border, the left X right gradient of area 18 was used, as myelin maps become unreliable in this region. The top row is the left hemisphere and the bottom row is the right hemisphere. Panels A and F show the myelin maps, panels B and G show the gradients of the myelin maps, panels C and H show gradients of the cortical areas shown in D and I (17, 18, and hOc5 (Amunts et al., 2000; Malikovic et al., 2007)) and panels E and J show the visotopic areas from Kolster et al (2010), Swisher et al (2007), and V6 of Pitzalis et al (2006). Two volumetrically mapped probabilistic areas (PGa and PGp (Caspers et al., 2006; Caspers et al., 2008)) are shown as 3D centers of gravity. For the visotopic maps, areas V1, V2, and V3 were not shown because they do not align with the histologically defined areas; see (D. C. Van Essen, M. F. Glasser, D. L. Dierker, J. Harwell, and T. Coalson, unpublished observations).
Figure 11:
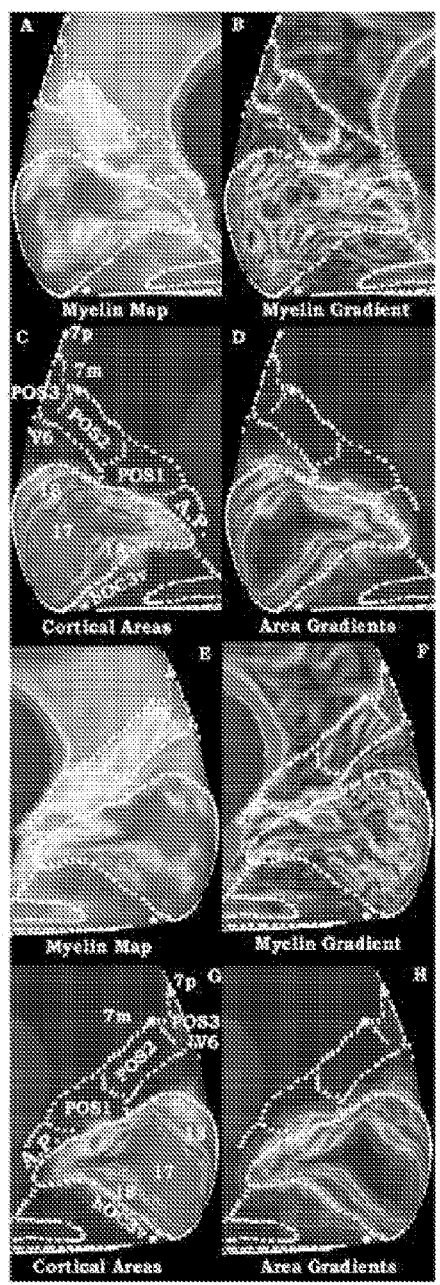
FIG. 11 shows myelin maps, gradients of myelin maps, cortical areas, and gradients of cortical areas of the medial visual cortex on an inflated surface. Similar to FIG. 10, the white marks are in the same location in both hemispheres and were defined similarly. The top two rows are the left hemisphere and the bottom two rows are the right hemisphere. Panels A and E show the myelin maps, panels B and F show the gradients of the myelin maps, panels C and G show the cortical areas, 17 and 18 from Amunts, et al. (2000), V6 from Pitzalis, et al. (2006), and hOC3v from Rottschy et al (2007) and panels D and H show the gradients of the area 18.
Figure 12:
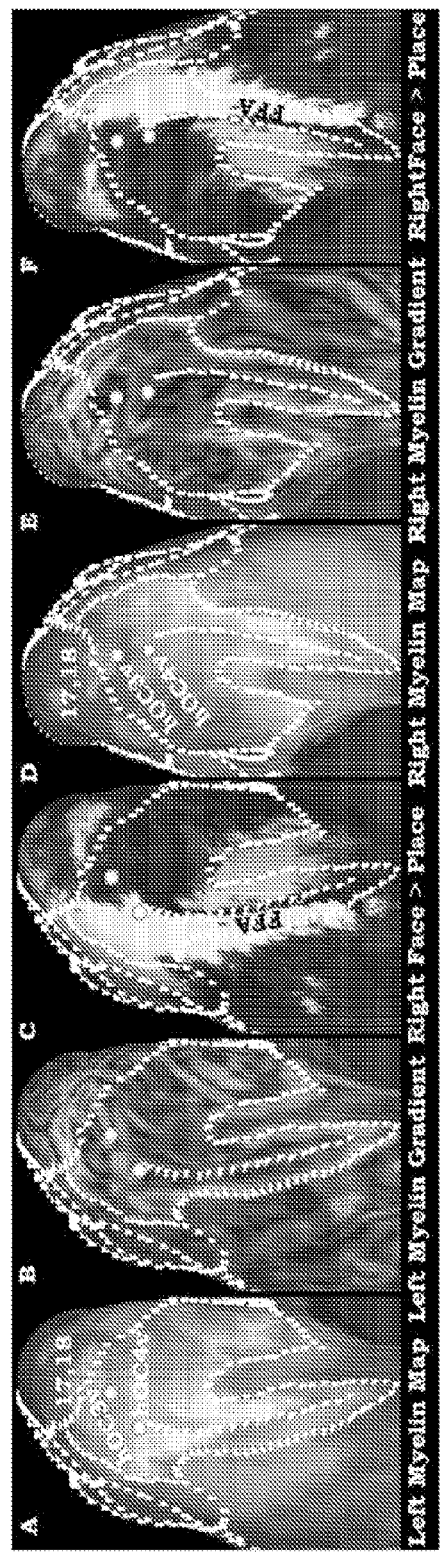
FIG. 12 shows myelin maps, gradients of myelin maps, and the group average right hemisphere results of Rajimehr et al (2009) on an inflated surface. Similar to FIG. 10 and FIG. 11, the white marks are in the same location in both hemispheres and were defined similarly. The first 3 panels are the left hemisphere and the second 3 are the right hemisphere. Panels A and D show the myelin maps and 3D centers of gravity of areas hOC3v and hOC4v from (Rottschy et al., 2007), panels B and E show the gradients of the myelin maps, and panels C and F show the Faces>Places task fMRI contrast of the right hemisphere from Rajimehr et al (2009).
Figure 13:
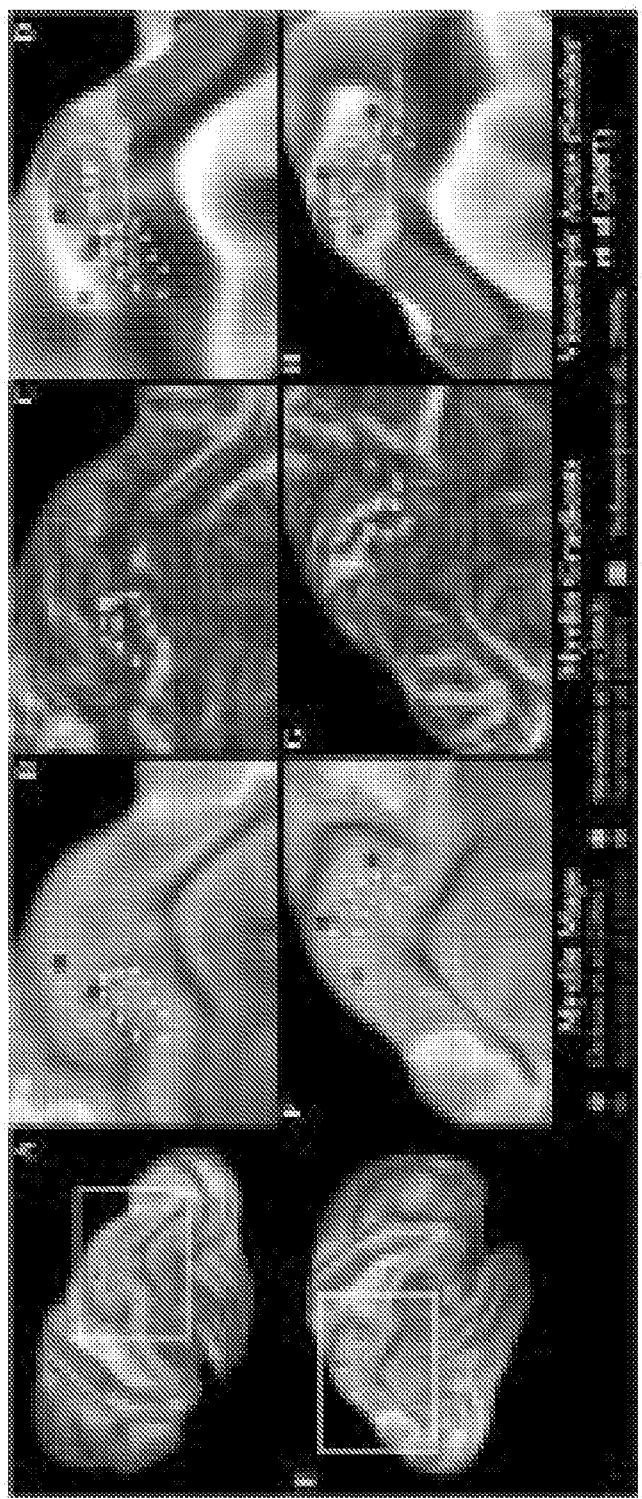
FIG. 13 shows myelin maps (A,B,E,F), gradients of myelin maps (C,G), and visotopic areas of (Swisher et al., 2007) of the left and right hemispheres (D,H) on an inflated surface. The top panels are the left hemisphere and the bottom panels are the right hemisphere. The most heavily myelinated IPS area is surrounded by white marks that are the same in each panel within a hemisphere. The ellipse surrounds the region that has been suggested to be the homologue of macaque area LIP by functional studies. The center of gravity of the nearby area hIP3 from (Scheperjans et al., 2008a) is also shown.
Figure 14:
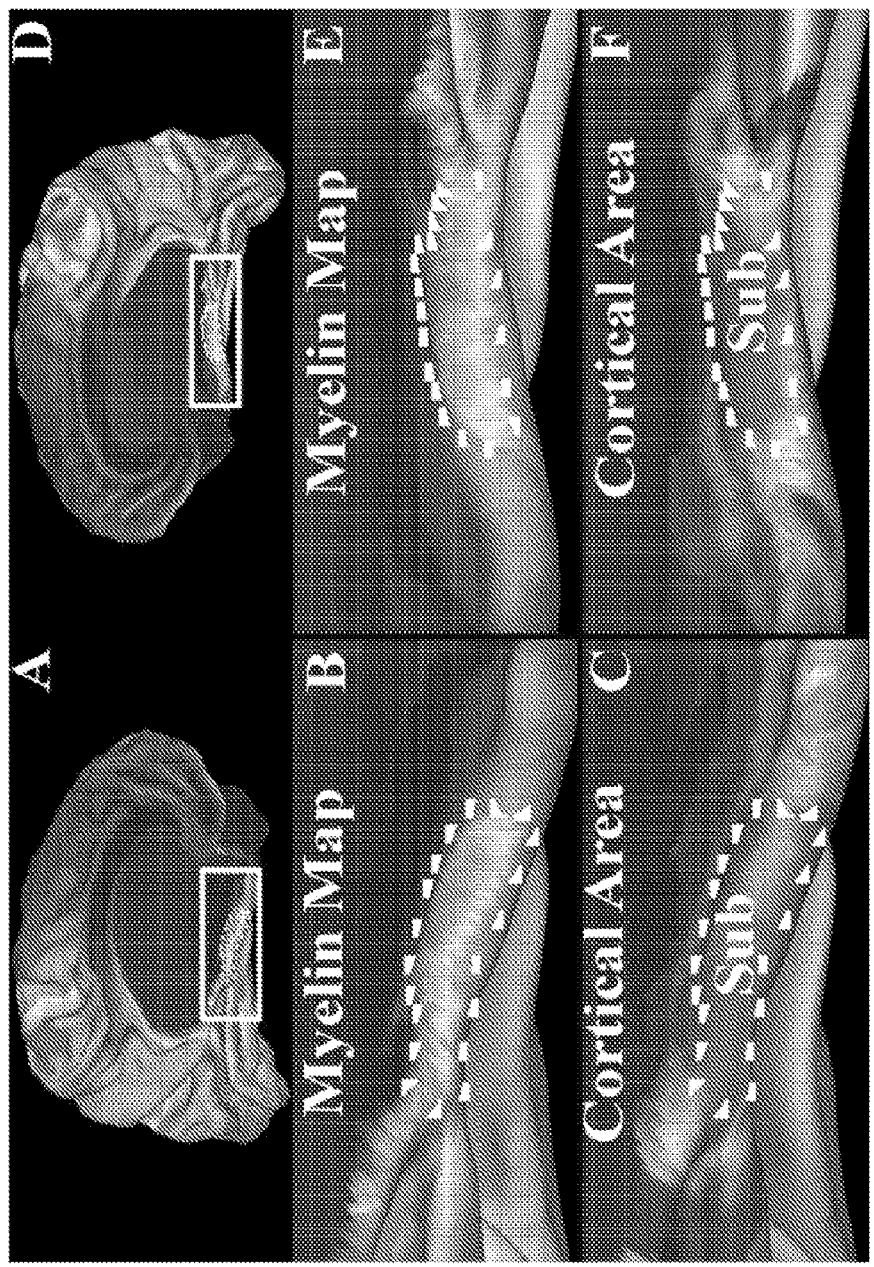
FIG. 14 shows myelin maps (B,E) and probabilistic cortical area (C,F) from (Amunts et al., 2005) on a cortical midthickness surface. Left hemisphere is the first column, and right hemisphere is the second column. The probabilistic area of the subiculum complex (Sub) is centered on the region of heavier myelination on the parahippocampal gyrus. The white marks are in the same locations in each panel within a hemisphere.
Figure 15:
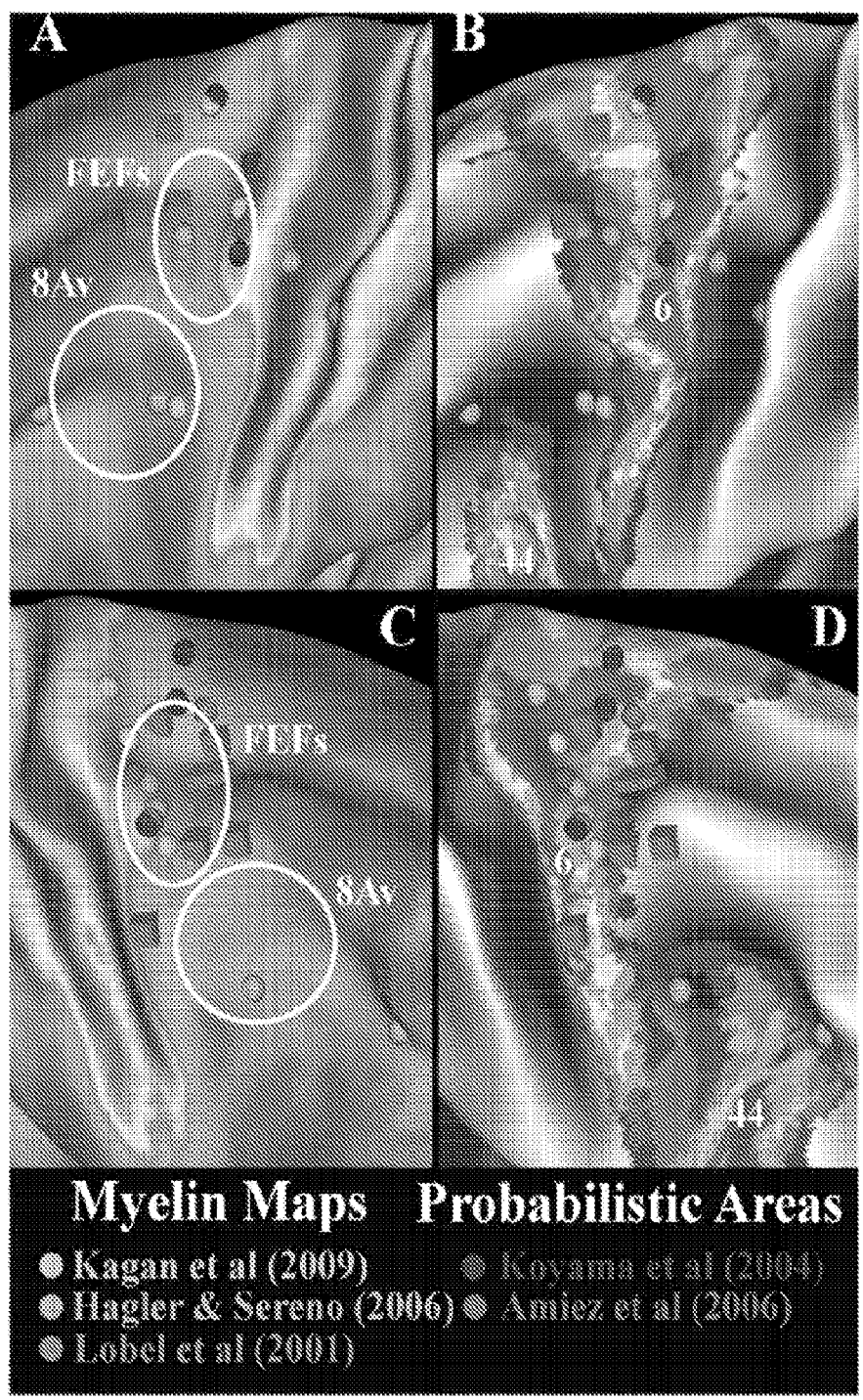
FIG. 15 shows myelin maps and probabilistic areas 6 from (Geyer, 2004) and 44 from (Amunts et al., 1999). The top panels are the left hemisphere and the bottom panels are the right hemisphere. Foci from several fMRI studies of regions activated by saccade tasks are shown for both hemispheres as spheres. One study, (Lobel et al., 2001) also used electrical stimulation to elicit saccades, and their stimulation coordinates are marked by cubes. The dorsal ellipse surrounds the region of overlap between fMRI activations, saccades elicited by stimulation, and moderate to heavy cortical myelination that is the most likely location of the FEFs. The ventral ellipse surrounds a region that may be area 8Av.
Figure 16:
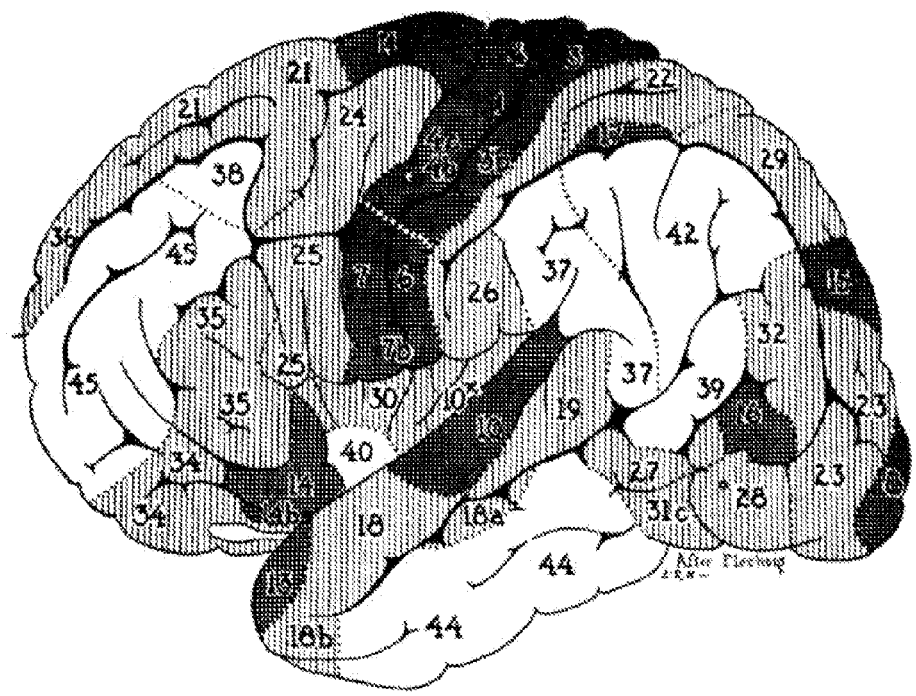
FIG. 16 shows maps of subcortical myelination during development by Flechsig modified by Von Bonin from Fuster 1995 (reproduced with permission). Darkly shaded regions myelinate first, then intermediate shaded regions myelinate, and finally unshaded regions myelinate last. The order of myelinatation is given by the numbers.
Figure 16:
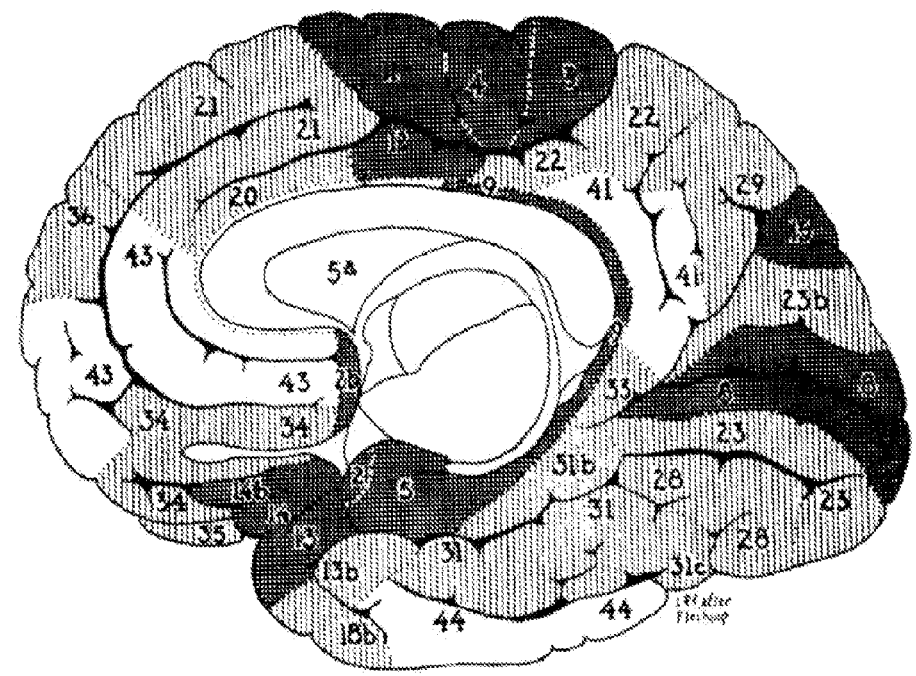

In volume slices of T1w and T2w images, interesting local signal inhomogeneities are evident in the grey matter, particularly in regions such as the central sulcus (FIG. 3A, FIG. 3B). These inhomogeneities are enhanced in the T1w/T2w ratio images (FIG. 3C). When a color palette is used instead of grey scale, the differences become even more apparent (FIG. 3D). The boundaries drawn on the colorized T1w/T2w image in FIG. 3D represent putative transitions between cortical areas (see Results). Indeed, a direct comparison between myelin stained histology and T1 contrast in the central sulcus reported a similar border between areas 4 and 3a that was aligned in both methodologies (Geyer et al., 2011).

Example 5: Surface-Based T1w/T2w Ratio Analysis

A customized volume-to-surface mapping algorithm was applied to voxels assigned to the grey matter ribbon by FreeSurfer i.e. those with voxel centers located between the white and pial surfaces. To preserve accuracy, the grey matter ribbon mask was not resampled once generated. For each vertex in the native mesh midthickness surface, ribbon voxels were selected within a cylinder orthogonal to the local surface. The cylinder had a height and radius equal to local cortical thickness value and was centered on the vertex.

Voxels were excluded if the T1w/T2w value exceeded +/− one standard deviation of all T1w/T2w values within the cortical ribbon. This criterion had the effect of removing voxels that contained significant blood vessel signal with very high T1w/T2w values or CSF signal with very low values. The remaining ribbon voxels were averaged according to a Gaussian weighted function (FWHM=~4 mm, sigma=5/3 mm) to produce a value for the vertex. Vertices in the non-cortical medial wall had a FreeSurfer thickness value of zero and were assigned a T1w/T2w value of zero.

Small patches of aberrant T1w/T2w values were detected and corrected as follows. Each vertex's cortical thickness and T1w/T2w values were compared to the mean values of the neighbors within 10 steps across the surface. If the values of both the cortical thickness and the T1w/T2w exceeded two standard deviations from the mean, it was assumed that an error had occurred in surface reconstruction and thus the data were unreliable. These values were replaced by a Gaussian-weighted average of their neighbors using a geodesic distance weighting. Only vertices having cortical thickness values and T1w/T2w values less than 2 standard deviations from the mean were included in the Gaussian weighted average (FWHM=~4 mm, sigma=5/3 mm). This outlier detection and correction method performed well at removing small artifacts from the data; however, it failed to correct larger ones. If the anomalies are large enough, they affect the neighborhood mean and standard deviation and no longer appear anomalous to the algorithm. The individual subject shown in FIG. 5C, FIG. 5F, FIG. 5I and FIG. 5L were processed with a standard deviation value of one. This yielded a modestly improved artifact correction, but at a large increase in computational time that precluded application to all 80 subjects. Finally, this individual's data were smoothed across the surface using a Gaussian average weighted by geodesic distance (FWHM=5 mm) that reduced high spatial frequency information, which appeared to be mostly noise. We intend to incorporate the myelin mapping software into Caret, and interested investigators should contact the corresponding author.

Example 6: Construction and Analysis of Group Average Data

Transformation of myelin map data from the individual subject's native mesh to the fs_LR standard mesh involves two deformation maps, one representing registration from the native mesh to fs_L and fs_R and another representing registration between fs_L and fs_R and fs_LR. The two deformation maps were concatenated into a single deformation map (D. C. Van Essen, M. F. Glasser, D. L. Dierker, J. Harwell, and T. Coalson, unpublished observations) that was applied to the individual subject's myelin map data, cortical thickness data, and surface curvature data. Average midthickness surfaces for the left and right hemispheres were generated from the individual subjects' registered surfaces, and these were strikingly similar to the $fs_{average}$ midthickness surfaces. The individual myelin map data were normalized to a group global mean and then averaged at each surface node. A small amount of geodesic Gaussian weighted smoothing was applied to the group average myelin map (FWHM=2.35 mm). The gradient magnitude i.e. the first spatial derivative of the group average myelin map was computed on the group average midthickness surface. This gradient provides an observer-independent measure of rapid transitions in myelin content and can be used as a basis for delineating areal borders. To avoid edge effects along the noncortical medial wall, this region was masked and the intensity along the edge was dilated into the center prior to computing the gradient. The gradient analyses used here are similar in spirit to those introduced by Cohen et al. (2008) and Nelson et al. (2010), but differ in implementation. Whereas they computed gradients on a Cartesian grid overlayed on a flat map (Cohen et al., 2008; Nelson et al., 2010), we computed gradients directly on the convoluted surface mesh, avoiding the necessary cuts and inherent distortions in the flattening process.

Example 7: Color Palette

Myelin map values are dimensionless quantities whose magnitude depends on many factors. The color palette used to display myelin maps was adjusted so that its dynamic range was most informative for identifying the transitions between adjacent areas that are also highlighted by the gradient calculation. Practically, the myelin maps (and other images) were displayed at 3rd and 96th percentiles for the hemisphere as a whole, with saturation above (red) and below (black) these values. FIG. 4 shows the image histograms for the Conte-69, NAMIC-10, and the individual subject datasets. The histograms are very similar in shape, with the highest peak representing the large expanses of lightly myelinated cortex and a smaller peak or hump representing the heavily myelinated regions of cortex. Although the absolute values are two-fold higher for NAMIC-10 vs Conte-69, the use of percentile scaling allows a direct comparison between them in FIG. 5.

Example 8: Thickness Maps

In addition to myelin maps and their gradients, cortical thickness maps and their gradients were also analyzed. Cortical thickness maps and surface curvature maps were averaged after resampling onto the fs_LR mesh. The average surface curvature was regressed out of the average cortical thickness map in a manner similar to Sigalovsky et al. (2006), thereby correcting the thickness map for biases caused by gyral and sulcal folding. The magnitude of the spatial gradient was computed on this curvature-compensated cortical thickness map with a prior smoothing of FWHM=2.35 mm.

Example 9: Probabilistic Cytoarchitectonic Areas and Activation Foci

Surface-based probabilistic cytoarchitectonic areas were obtained from the standard FreeSurfer distribution, most of which were described in (Fischl et al., 2008). Spatial gradient magnitudes were computed for each probabilistic cytoarchitectonic area as an observer-independent measure of its most likely average border. Volume-based cytoarchitectonic areas were obtained from the SPM Anatomy Toolbox (Eickhoff et al., 2005a) and were transformed from the original Colin27 space into the $fs_{average}$ volume space for accurate mapping to the $fs_{average}$ atlas surfaces. This entailed linear (FLIRT) followed by nonlinear (FNIRT) registration of Colin27 to the MNI152 nonlinearly generated template distributed with FSL. The $fs_{average}$ average volume was also linearly and then nonlinearly registered to the MNI152 template. This transformation was inverted and concatenated to the Colin27-to-MNI152 transform to produce a Colin27-to-$fs_{average}$ nonlinear transform. The transform was then applied to the probabilistic architectonic volumes using nearest neighbor resampling to preserve the actual probability values. The volumetric maps were mapped to the fs_LR midthickness surface using Caret's interpolated voxel method. Because these maps do not respect the topology of the cortical sheet, spatial gradients would not be meaningful as they are for surface-based probabilistic areas and thus were not computed. In some cases, volumetric maps were represented by foci located at their centers of gravity, or as a hard segmentation. Hard segmentations were produced by thresholding the volumetric probabilistic cortical areas at a value that reflected 40% of subjects and then assigning each voxel to the cortical area having the highest probability. Published coordinates of functional activation foci were used in their reported MINI coordinates or after conversion from the Talairach coordinates using a Matlab script (http://imaging.mrc-cbu.cam.ac.uk/imaging/MniTalairach). Functional activation maps and parcellations were mapped onto the fs_LR surfaces as described in (D. C. Van Essen, M. F. Glasser, D. L. Dierker, J. Harwell, and T. Coalson, unpublished observations).

Example 10: Delineation of Corresponding Locations Along Putative Areal Borders The highlighted surface vertices (white squares) in FIGS. 5-14 are in corresponding locations in each panel. They were positioned using information in the myelin gradients, probabilistic areal gradients, and/or thickness gradients, unless otherwise specified. They are positioned to reveal the correlations across the different modalities in the panels. They also indicate areal borders (when the identity of an area is known from histological studies mapped onto the surface) or putative areal borders when the areal identity is inferred from published figures. They are not intended to create a "hard" segmentation of cortex into distinct parcels; rather, they draw attention to myelin features that likely represent distinct cortical areas. The magnitude and width of the myelin gradient represents how distinct one feature is from another and how quickly the myelin content changes.

Example 11: Myelin Content Surface Maps of Adolf Hopf

Adolf Hopf produced some of the most detailed myeloarchitectonic parcellations of human cortex (Zilles, 2004). Unfortunately, most of these results were published in German in a now defunct journal and are rarely cited. Hopf produced drawings of what appear to be surface maps of myelin content for temporal (Hopf, 1955), frontal (Hopf, 1956), and parietal (Hopf and Vitzthum, 1957) cortices. Maps of cingulate cortex are also included together with frontal and parietal cortex (Hopf, 1956; Hopf and Vitzthum, 1957).

Example 12: MRW Metric Comparison

This study consisted of 23 controls (aged 46.6±9.86; 12 females) and 92 patients (aged 51.2±9.54; 53 females). All subjects were scanned in a Siemens 3T Skyra with a 20-channel neck-head coil. The scans were acquired with the following parameters: 3D MPRAGE (sagittal acquisition, 1 mm$^3$ cubic voxel, TR/TE/TI: 2300 ms/2.98 ms/900 ms, angle 9°), 3D FLAIR (sagittal acquisition, 1 mm$^3$ cubic voxel, TR/TE/TI: 5000 ms/389 ms/1800 ms), Magnetization transfer (2.2 kHz off-resonance pulse; flip angle=5°; TR/TE=29/5; resolution=1.25 mm isotropic) and diffusion tensor (b=2000; 64 directions; TR/TE=7700/96; resolution=2.2 mm isotropic) images were also acquired and processed for all patients.

Image Processing

Each subject's T2-FLAIR image was registered to its corresponding T1w image using FSL's FLIRT (Jenkinson et al., 2002). The registered image was then divided by the T1 and scaled by a constant factor. All ratio images were then [affine] linearly and nonlinearly registered to the MNI152 2 mm standard space using FSL'S FLIRT and FNIRT (Andersson et al., 2010) respectively.

In the common space, a voxel-wise multivariate regression was run on the control data using age and gender as covariates, resulting in coefficient maps. A voxel-wise difference map was then generated for each subject (patients and controls) by subtraction of the predicted MRW value for that subject (for example based on age and gender from the multivariate regression).

A standard error map was created by computing the voxel-wise standard deviation of the difference map values across the reference subjects. Z-score maps were created for all cases and reference subjects by dividing their difference map by the standard error map.

DTI was pre-processed using FSL's eddy correct, and metrics were then calculated using (Garyfallidis et al., 2014) to obtain FA, RD, MD, and AD. MT data was processed as described by Helms et al., (2008).

T2-FLAIR lesions were segmented using a semi-automatic procedure. These lesion masks were used in FSL's SIENAX (Smith et al., 2002) segmentation through which white matter, grey matter, and whole brain masks were obtained. The white matter mask was then separated into lesion, dirty white matter (DWM) defined as the one centimeter around lesions and normal-appearing white matter (NAWM) masks.

Statistics

QQ-plots were used to confirm normal distributions for each metric. Pearson and Spearman correlations were used to determine the relationship between clinical and imaging metrics. Linear regression and partial least squares regression (PLS) were used to compare imaging metrics' abilities to predict clinical metrics. FDR correction was used for multiple comparisons.

Results

In all regions of interest, the MRW T2/T1 z-score correlated best with diffusion tensor metrics though correlations with MTR were also high. Gray matter MRW z-scores were most correlated with mean diffusivity (r=0.64) and MTR (r=−0.43). Normal-appearing white matter had MRW z-scores were inversely correlated with fractional anisotropy having an r=−0.53 and MTR with an r=−0.44. In pathological tissue (dirty white matter and focal lesions), MRW z-scores were inversely correlated with MTR (r=−0.40 and r=−0.32 respectively) and positively correlated with mean diffusivity (r=0.64 and 0.52 respectively). Unlike in normal-appearing white matter, MRW z-scores of dirty white matter and focal lesions were not correlated with fractional anisotropy at all (r=−0.13 and r=0.06).

Table 1 illustrates Correlation coefficients for MRW T2/T1 z-scores with advanced quantitative metrics.

TABLE 1

|  | MD | FA | MTR | T1 |
| --- | --- | --- | --- | --- |
| GM | 0.64 | 0.00 | −0.43 | 0.05 |
| NAWM | 0.50 | −0.53 | −0.44 | 0.30 |

TABLE 1-continued

|  | MD | FA | MTR | T1 |
|---|---|---|---|---|
| DWM | 0.64 | −0.13 | −0.40 | 0.56 |
| LESIONS | 0.52 | 0.06 | −0.32 | 0.51 |

Table 2 is Correlation coefficients for MRW T2/T1 z-scores with EDSS.

TABLE 2

|  | MRW z | MD | FA | MTR | T1 |
|---|---|---|---|---|---|
| GM | 0.35 | 0.27 | −0.11 | −0.19 | 0.04 |
| NAWM | 0.28 | 0.10 | −0.18 | −0.23 | 0.02 |
| DWM | 0.20 | 0.16 | −0.32 | −0.32 | 0.03 |
| Lesions | 0.14 | 0.17 | −0.15 | −0.25 | 0.14 |

The T2/T1 average z-score in the gray matter showed the highest correlation with EDSS (r=0.35) and disease duration (r=0.24). EDSS showed a negative Pearson's r of −0.32 with both MTR and FA of the dirty white matter. For disease duration, close runners-up were AD of the gray matter (r=0.22) and lesion FA (r=0.21).

Discussion

DTI measures the anisotropy of water movement in tissues and produces four metrics of interest: fractional anisotropy (FA), mean diffusivity (MD), axial diffusivity (AD), and radial diffusivity (RD). Changes in FA and AD have been shown to reflect axonal damage, and RD increase has been shown to reflect myelin breakdown. Abnormal DTI values have been found throughout the brain in all stages of MS (Rovaris et al., 2009).

MT imaging assesses macromolecular signal with the application of on- and off-resonance pulses. The MT ratio (MTR), which is derived from the differences between the resulting images, reflects macromolecular content. The relationship between MTR and myelin content in MS lesions over time has been summarized by Chen et al. (2008). Changes in MTR were shown to reflect demyelination and remyelination of gadolinium-enhancing lesions. Like in DTI, decreased MTR in NAWM has been found to predict likely sites of developing T2 lesions (Filippi et al., 1998a; Goodkin et al., 1998; Fazekas et al., 2002).

As previously stated, MRW imaging is not a marker of specific pathological processes but of general dysfunction/tissue damage. Because tissue relaxation times are affected by a multitude of factors in varying ways e.g., increase in iron causes decreases T2, whereas decreased presence of macromolecules has the opposite effect changes in MRW intensity. In that sense, sequences like DTI and MT may still provide more information. Black holes also have lower MTR values than T1 isointense lesions (Hiehle et al., 1995; van Waesberghe et al., 1998) and " . . . MTR is inversely correlated with the degree of hypointensity (Hiehle et al., 1995)."

Example 13: Thresholded T2/T1 z-Scores are a Viable Substitute for T2 Lesion Volume Multiple sclerosis (MS) is an autoimmune disease characterized by the formation of lesions in the brain, particularly in the white matter. The gold standard for lesion segmentation remains manual segmentation; however the process is both time-consuming and subjective. Numerous semi-automatic methods exist, but all require manual corrections. A fully automated method that provides an alternative to manually edited lesion masks for lesion segmentation was analyzed.

Methods

Zscores were obtained as detailed by Example 1. Prior information was used in MINI space to determine each voxel's tissue probability. Any voxel that had more than a 10% probability of being gray matter or cerebrospinal fluid was discarded from consideration. The z-score images were thresholded at 0, 5, and 10. These values were chosen based on the average zscores of lesions found in the previous example.

The T2/T1 metric is normalized either via phantom scans of the sequences or knowledge of the scaling factors. If acquisition parameters are not held constant then pseudo-normalization can is also done using phantom scans with multiple relaxation times. Normalization is also possible using internal reference to non-changing structures in the field of view. Decile normalization method by Nyul, 2000 as validated for MS by Shah, 2011.

Derived Metrics

In addition to the MRW and MRW z-score maps, volumes defined by set thresholds are also generated to quantify the volume of affected tissue. For example, MS lesions can be identified above a threshold, and the volume of such lesions quantified. The analyses can be restricted to specific tissue types, for example white matter, by use of masks over those regions. Other metrics include the volumes defined by a set of z-score thresholds (e.g. −10, −5, 0, 5, 10) in the white matter, gray matter, and whole brain.

Results

Brain volume differences between the two SIENAX runs were <1%, which is the scan-rescan reliability reported by (source) lesion volume/count correlations/RSQ (Pearson correlation of 0.9 and RSQ of 0.82), dice coefficients (70s), icc (80ish) genetics correlations voxel count of white matter z-scores thresholded at 5 and 10 standard deviations (SDs) displayed high correlations to T2 lesion volume with RSQ values of 0.57 and 0.54 respectively. Stepwise multivariate regression including volume above T2/T1 ratio of 5 SDs, T2 lesion volumes, and whole brain volume selected only brain volume and T2/T1 ratio volume to be important in predicting EDSS score, and not T2 lesion volume. Voxel-wise correlation maps with EDSS versus T2/T1 ratio z-score showed notable regionality with higher spearman correlations around the ventricles and frontal white matter while correlations with the clinical brainstem scores indicated clusters in the brainstem and motor pathways.

These maps provide use as quantitative metrics to characterize tissue changes in disease and health. In particular they enable a new method of defining MS lesions that provides object levels of demarcation. Furthermore, these data provide there is richer and more information data regarding the load of disease burden since using varying thresholds (based either on MRW values or z-scores) to define the levels of tissue change.

These maps provide a myelin-weighted metric within the brain and correlate with MR relaxation times, magnetization transfer, and diffusion MRI metrics.

The data used to create these maps are routinely acquired in clinical MRI protocol for subjects with neurological imaging.

The T2/T1 ratio z-score shows itself to be a new metric in predicting clinical scores superior to T2 lesion load. With further validation, it can allow for better tracking and prediction of patients' disease progression and will allow for retrospective studies as T2 and T1 scans are and have been common place, as opposed to a new metric from a new pulse sequence.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Andersson J L R, Jenkinson M, Smith S (2010) Non-linear registration, aka spatial normalisation. FMRIB technical report TR07JA2
2. Chen et al. 2008
3. Fazekas et al., 2002
4. Filippi et al., 1998a
5. Garyfallidis E, Brett M, Amirbekian B, Rokem A, van der Walt S, Descoteaux M, Nimmo-Smith I and Dipy Contributors (2014). *Dipy, a library for the analysis of diffusion MRI data*. Frontiers in Neuroinformatics, vol. 8, no. 8.
6. Glasser M F, Van Essen D C. Mapping Human Cortical Areas in vivo Based on Myelin Content as Revealed by T1- and T2-weighted MRI. J Neurosci 2011; 31(32): 11597-11616.
7. Goodkin et al., 1998
8. Jenkinson, M., Bannister, P., Brady, J. M. and Smith, S. M. Improved Optimisation for the Robust and Accurate Linear Registration and Motion Correction of Brain Images. NeuroImage, 17(2), 825-841, 2002.
9. Miller, 1998
10. Ramli, 2010
11. S. M. Smith, Y. Zhang, M. Jenkinson, J. Chen, P. M. Matthews, A. Federico, and N. De Stefano. Accurate, robust and automated longitudinal and cross-sectional brain change analysis. NeuroImage, 17(1):479-489, 2002.
12. Glasser et al. (2011) "Mapping Human Cortical Areas In Vivo Based on Myelin Content as Revealed by T1- and T2-Weighted MRI" J. of Neuroscience 31(32):11597-11616.
13. U.S. Pat. No. 7,657,299
14. Amiez C, Petrides M. Anatomical organization of the eye fields in the human and non-human primate frontal cortex. Progress in neurobiology. 2009; 89:220-230. [PubMed: 19665515]
15. Amiez C, Kostopoulos P, Champod A S, Petrides M. Local morphology predicts functional organization of the dorsal premotor region in the human brain. Journal of Neuroscience. 2006; 26:2724. [PubMed: 16525051]
16. Amunts K, Malikovic A, Mohlberg H, Schormann T, Zilles K. Brodmann's Areas 17 and 18 Brought into Stereotaxic Space—Where and How Variable? Neuroimage. 2000; 11:66-84. [PubMed: 10686118]
17. Amunts K, Schleicher A, Bürge U, Mohlberg H, Uylings H, Zilles K. Broca's region revisited: cytoarchitecture and intersubject variability. The Journal of comparative neurology. 1999; 412:319-341. [PubMed: 10441759]
18. Amunts K, Lenzen M, Friederici A, Schleicher A, Morosan P, Palomero-Gallagher N, Zilles K. Broca's Region: Novel Organizational Principles and Multiple Receptor Mapping. PLoS Biology. 2010; 8:330-357.
19. Amunts K, Kedo O, Kindler M, Pieperhoff P, Mohlberg H, Shah N, Habel U, Schneider F, Zilles K. Cytoarchitectonic mapping of the human amygdala, hippocampal region and entorhinal cortex: intersubject variability and probability maps. Anatomy and Embryology. 2005; 210: 343-352. [PubMed: 16208455]
20. Augustinack J, Helmer K, Huber K, Kakunoori S, Zöllei L, Fischl B. Direct Visualization of the Perforant Pathway in the Human Brain with Ex Vivo Diffusion Tensor Imaging. Frontiers in Human Neuroscience. 2010:4. [PubMed: 20198130]
21. Barbas H, Pandya D N. Architecture and intrinsic connections of the prefrontal cortex in the rhesus monkey. The Journal of comparative neurology. 1989; 286:353-375. [PubMed: 2768563]
22. Barbier E, Marrett S, Danek A, Vortmeyer A, van Gelderen P, Duyn J, Bandettini P, Grafman J, Koretsky A. Imaging cortical anatomy by high-resolution MR at 3.0 T: detection of the stripe of Gennari in visual area 17. Magnetic Resonance in Medicine. 2002; 48:735-738. [PubMed: 12353293]
23. Belmalih A, Borra E, Contini M, Gerbella M, Rozzi S, Luppino G. Multimodal architectonic subdivision of the rostral part (area F5) of the macaque ventral premotor cortex. The Journal of comparative neurology. 2009; 512:183-217. [PubMed: 19003790]
24. Blanke O, Spinelli L, Thut G, Michel C M, Perrig S, Landis T, Seeck M. Location of the human frontal eye field as defined by electrical cortical stimulation: anatomical, functional and electrophysiological characteristics. Neuroreport. 2000; 11:1907. [PubMed: 10884042]
25. Bock N, Kocharyan A, Liu J, Silva A. Visualizing the entire cortical myelination pattern in marmosets with magnetic resonance imaging. Journal of neuroscience methods. 2009; 185:15-22. [PubMed: 19737577]
26. Braak H. The pigment architecture of the human occipital lobe. Anatomy and Embryology. 1977; 150:229-250. [PubMed: 857702]
27. Braak H. The pigment architecture of the human temporal lobe. Anatomy and Embryology. 1978; 154:213-240. [PubMed: 686398]
28. Braak H. Pigment architecture of the human telencephalic cortex. IV. Regio retrosplenialis. Cell and tissue research. 1979a; 204:431. [PubMed: 527027]
29. Braak H. The pigment architecture of the human frontal lobe. Anatomy and Embryology. 1979b;
30. 157:35-68. [PubMed: 517758]
31. Braak H. Pigment architecture of the human telencephalic cortex. V. Regio anterogenualis. Cell and tissue research. 1979c; 204:441. [PubMed: 527028]
32. Bridge H, Clare S, Jenkinson M, Jezzard P, Parker A, Matthews P. Independent anatomical and functional measures of the V1/V2 boundary in human visual cortex. Journal of Vision. 2005:5.
33. Brodmann, K. Vergleichende Lokalisationslehre der Grosshirnrinde in ihren Prinzipien dargestellt auf Grund des Zellenbaues. Barth Leipzig; 1909.
34. Brodmann, K.; Garey, L. Brodmann's Localisation in the cerebral cortex: the principles of comparative localisation in the cerebral cortex based on the cytoarchitectonics. Springer Verlag; 2006.
35. Burman K J, Rosa M G P. Architectural subdivisions of medial and orbital frontal cortices in the marmoset monkey (Callithrix jacchus). The Journal of comparative neurology. 2009; 514:11-29. [PubMed: 19260047]
36. Caspers S, Geyer S, Schleicher A, Mohlberg H, Amunts K, Zilles K. The human inferior parietal cortex: cytoarchitectonic parcellation and interindividual variability. Neuroimage. 2006; 33:430-448. [PubMed: 16949304]

37. Caspers S, Eickhoff S, Geyer S, Scheperjans F, Mohlberg H, Zilles K, Amunts K. The human inferior parietal lobule in stereotaxic space. Brain Structure and Function. 2008; 212:481-495. [PubMed: 18651173]
38. Clare S, Bridge H. Methodological issues relating to in vivo cortical myelography using MRI. Human brain mapping. 2005; 26:240-250. [PubMed: 15954140]
39. Clark V, Courchesne E, Grafe M. In vivo myeloarchitectonic analysis of human striate and extrastriate cortex using magnetic resonance imaging. Cerebral Cortex. 1992; 2:417. [PubMed: 1422094]
40. Clarke S. Modular organization of human extrastriate visual cortex: evidence from cytochrome oxidase pattern in normal and macular degeneration cases. European Journal of Neuroscience. 1994; 6:725-736. [PubMed: 8075817]
41. Clarke S, Miklossy J. Occipital cortex in man: Organization of callosal connections, related myelo and cytoarchitecture, and putative boundaries of functional visual areas. The Journal of comparative neurology. 1990; 298: 188-214. [PubMed: 2212102]
42. Cohen A L, Fair D A, Dosenbach N U F, Miezin F M, Dierker D, Van Essen D C, Schlaggar B L, Petersen S E. Defining functional areas in individual human brains using resting functional connectivity MRI. Neuroimage. 2008; 41:45-57. [PubMed: 18367410]
43. Collins C E, Airey D C, Young N A, Leitch D B, Kaas J H. Neuron densities vary across and within cortical areas in primates. Proceedings of the National Academy of Sciences. 2010; 107:15927.
44. Coq J O, Qi H, Collins C E, Kaas J H. Anatomical and functional organization of somatosensory areas of the lateral fissure of the New World titi monkey (Callicebus moloch). The Journal of comparative neurology. 2004; 476:363-387. [PubMed: 15282711]
45. Dale A, Fischl B, Sereno M. Cortical Surface-Based Analysis* 1:: I. Segmentation and Surface Reconstruction. Neuroimage. 1999; 9:179-194. [PubMed: 9931268]
46. De Araujo I, Rolls E, Kringelbach M, McGlone F, Phillips N. Taste olfactory convergence, and the representation of the pleasantness of flavour, in the human brain. European Journal of Neuroscience. 2003; 18:2059-2068. [PubMed: 14622239]
47. Ding S, Van Hoesen G, Cassell M, Poremba A. Parcellation of human temporal polar cortex: a combined analysis of multiple cytoarchitectonic, chemoarchitectonic, and pathological markers. The Journal of comparative neurology. 2009; 514:595-623. [PubMed: 19363802]
48. Disbrow E, Litinas E, Recanzone G, Padberg J, Krubitzer L. Cortical connections of the second somatosensory area and the parietal ventral area in macaque monkeys. The Journal of comparative neurology. 2003; 462: 382-399. [PubMed: 12811808]
49. Dum R P, Strick P L. The origin of corticospinal projections from the premotor areas in the frontal lobe. Journal of Neuroscience. 1991; 11:667. [PubMed: 1705965]
50. Eickhoff S, Schleicher A, Zilles K, Amunts K. The human parietal operculum. I. Cytoarchitectonic mapping of subdivisions. Cerebral Cortex. 2006a; 16:254. [PubMed: 15888607]
51. Eickhoff S, Amunts K, Mohlberg H, Zilles K. The human parietal operculum. II. Stereotaxic maps and correlation with functional imaging results. Cerebral Cortex. 2006b; 16:268. [PubMed: 15888606]
52. Eickhoff S, Stephan K, Mohlberg H, Grefkes C, Fink G, Amunts K, Zilles K. A new SPM toolbox for combining probabilistic cytoarchitectonic maps and functional imaging data. Neuroimage. 2005a; 25:1325-1335. [PubMed: 15850749]
53. Eickhoff S, Walters N, Schleicher A, Kril J, Egan G, Zilles K, Watson J, Amunts K. High resolution MRI reflects myeloarchitecture and cytoarchitecture of human cerebral cortex. Human brain mapping. 2005b; 24:206-215. [PubMed: 15543596]
54. Eickhoff S B, Weiss P H, Amunts K, Fink G R, Zilles K. Identifying human parieto-insular vestibular cortex using fMRI and cytoarchitectonic mapping. Human brain mapping. 2006c; 27:611-621. [PubMed: 16281284]
55. Elston G N, Benavides-Piccione R, DeFelipe J. The pyramidal cell in cognition: a comparative study in human and monkey. Journal of Neuroscience. 2001; 21:163.
56. Epstein R, Harris A, Stanley D, Kanwisher N. The Parahippocampal Place Area:: Recognition, Navigation, or Encoding? Neuron. 1999; 23:115-125. [PubMed: 10402198]
57. Fatterpekar G, Naidich T, Delman B, Aguinaldo J, Gultekin S, Sherwood C, Hof P, Drayer B, Fayad Z. Cytoarchitecture of the human cerebral cortex: MR microscopy of excised specimens at 9.4 Tesla. American Journal of Neuroradiology. 2002; 23:1313. [PubMed: 12223371]
58. Fischl B, Dale A. Measuring the thickness of the human cerebral cortex from magnetic resonance images. Proceedings of the National Academy of Sciences of the United States of America. 2000; 97:11050. [PubMed: 10984517]
59. Fischl B, Sereno M, Dale A. Cortical Surface-Based Analysis* 1:: II: Inflation, Flattening, and a Surface-Based Coordinate System. Neuroimage. 1999a; 9:195-207. PubMed: 9931269]
60. Fischl B, Liu A, Dale A. Automated manifold surgery: constructing geometrically accurate and topologically correct models of the human cerebral cortex. Medical Imaging, IEEE Transactions on. 2002; 20:70-80.
61. Fischl B, Sereno M, Tootell R, Dale A. High-resolution intersubject averaging and a coordinate system for the cortical surface. Human brain mapping. 1999b; 8:272-284. [PubMed: 10619420]
62. Fischl B, Salat D, van der Kouwe A, Makris N, Ségonne F, Quinn B, Dale A. Sequence-independent segmentation of magnetic resonance images. Neuroimage. 2004; 23:S69-S84. [PubMed: 15501102]
63. Fischl B, Rajendran N, Busa E, Augustinack J, Hinds O, Yeo B, Mohlberg H, Amunts K, Zilles K. Cortical Folding Patterns and Predicting Cytoarchitecture. Cerebral Cortex. 2008; 18:1973. [PubMed: 18079129]
64. Fukunaga M, Li T Q, van Gelderen P, de Zwart J A, Shmueli K, Yao B, Lee J, Maric D, Aronova M A, Zhang G. Layer-specific variation of iron content in cerebral cortex as a source of MRI contrast. Proceedings of the National Academy of Sciences. 2010; 107:3834.
65. Fuster, J M. Gradients of Cortical Plasticity. In: McGaugh, J L.; Weinberger, N M.; Lynch, G., editors. Brain and memory: modulation and mediation of neuroplasticity. Oxford University Press; USA: 1995.
66. Fuster J M. Network memory. Trends in Neurosciences. 1997; 20:451-459. [PubMed: 9347612] Georgieva S, Peeters R, Kolster H, Todd J T, Orban G A. The processing of three-dimensional shape from disparity in the human brain. The Journal of Neuroscience. 2009; 29:727. [PubMed: 19158299]

67. Geyer S. The microstructural border between the motor and the cognitive domain in the human cerebral cortex. Advances in anatomy, embryology, and cell biology. 2004:174.
68. Geyer S, Schleicher A, Zilles K. Areas 3a, 3b, and 1 of Human Primary Somatosensory Cortex:: 1. Microstructural Organization and Interindividual Variability. Neuroimage. 1999; 10:63-83. [PubMed: 10385582]
69. Geyer S, Schormann T, Mohlberg H, Zilles K. Areas 3a, 3b, and 1 of Human Primary Somatosensory Cortex: 2. Spatial Normalization to Standard Anatomical Space. Neuroimage. 2000; 11:684-696. [PubMed: 10860796]
70. Geyer S, Weiss M, Reimann K, Lohmann G, Turner R. Microstructural parcellation of the human cerebral cortex? from Brodmann's post-mortem map to in vivo mapping with high-field magnetic resonance imaging. Frontiers in Human Neuroscience. 2011; 5:5. [PubMed: 21441977]
71. Geyer S, Ledberg A, Schleicher A, Kinomura S, Schormann T, Bürgel U, Klingberg T, Larsson J, Zilles K, Roland P E. Two different areas within the primary motor cortex of man. 1996
72. Glasser M, Rilling J. DTI tractography of the human brain's language pathways. Cerebral Cortex. 2008; 18:2471. [PubMed: 18281301]
73. Glasser, M.; Laumann, T.; Coalson, T.; Cohen, A.; Snyder, A.; Schlaggar, B.; Petersen, S.; Van Essen, D. Organization for Human Brain Mapping. Quebec City: 2011. Comparison of Surface Gradients Derived from Myelin Maps and Functional Connectivity Analysis.
74. Grefkes C, Fink G. The functional organization of the intraparietal sulcus in humans and monkeys. Journal of Anatomy. 2005; 207:3-17. [PubMed: 16011542]
75. Grefkes C, Geyer S, Schormann T, Roland P, Zilles K. Human somatosensory area 2: observer-independent cytoarchitectonic mapping, interindividual variability, and population map. Neuroimage. 2001; 14:617-631. [PubMed: 11506535]
76. Hackett T, Preuss T, Kaas J. Architectonic identification of the core region in auditory cortex of macaques, chimpanzees, and humans. The Journal of comparative neurology. 2001; 441:197-222. [PubMed: 11745645]
77. Hagler D J Jr, Sereno M I. Spatial maps in frontal and prefrontal cortex. Neuroimage. 2006; 29:567-577. [PubMed: 16289928]
78. Hansen K A, Kay K N, Gallant J L. Topographic organization in and near human visual area V4. The Journal of Neuroscience. 2007; 27:11896. [PubMed: 17978030]
79. He S, Dum R, Strick P. Topographic organization of corticospinal projections from the frontal lobe: motor areas on the medial surface of the hemisphere. The Journal of Neuroscience. 1995; 15:3284-3306. [PubMed: 7538558]
80. He S Q, Dum R P, Strick P L. Topographic organization of corticospinal projections from the frontal lobe: motor areas on the lateral surface of the hemisphere. Journal of Neuroscience. 1993; 13:952. [PubMed: 7680069]
81. Hill J, Inder T, Neil J, Dierker D, Harwell J, Van Essen D. Similar patterns of cortical expansion during human development and evolution. Proceedings of the National Academy of Sciences. 2010; 107:13135.
82. Hinds O, Polimeni J R, Rajendran N, Balasubramanian M, Amunts K, Zilles K, Schwartz E L, Fischl B, Triantafyllou C. Locating the functional and anatomical boundaries of human primary visual cortex. Neuroimage. 2009; 46:915-922. [PubMed: 19328238]
83. Hopf A. Über die Verteilung myeloarchitektonischer Merkmale in der isokortikalen Schläfenlappenrinde beim Menschen'). J Hirnforsch. 1955; 2:36-54.
84. Hopf A. Über die Verteilung myeloarchitektonischer Merkmale in der Stirnhirnrinde beim Menschen. J Hirnforsch. 1956; 2:311-333. [PubMed: 13376888]
85. Hopf A, Vitzthum H G. ÜOber die Verteilung myeloarchitektonischer Merkmale in der Scheitellappenrinde beim Menschen. JOURNAL FÜR HIRNFORSCHUNG. 1957:3.
86. Huk A C, Dougherty R F, Heeger D J. Retinotopy and functional subdivision of human areas MT and MST. Journal of Neuroscience. 2002; 22:7195. [PubMed: 12177214]
87. Ino T, Inoue Y, Kage M, Hirose S, Kimura T, Fukuyama H. Mental navigation in humans is processed in the anterior bank of the parieto-occipital sulcus. Neuroscience letters. 2002; 322:182-186. [PubMed: 11897168]
88. Jenkinson M, Bannister P, Brady M, Smith S. Improved optimization for the robust and accurate linear registration and motion correction of brain images. Neuroimage. 2002; 17:825-841. [PubMed: 12377157]
89. Johansen-Berg H, Behrens T, Robson M, Drobnjak I, Rushworth M, Brady J, Smith S, Higham D, Matthews P. Changes in connectivity profiles define functionally distinct regions in human medial frontal cortex. Proceedings of the National Academy of Sciences of the United States of America. 2004; 101:13335. [PubMed: 15340158]
90. Kagan I, Iyer A, Lindner A, Andersen R A. Space representation for eye movements is more contralateral in monkeys than in humans. Proceedings of the National Academy of Sciences. 2010; 107:7933.
91. Kim E Y, Kim D H, Chang J H, Yoo E, Lee J W, Park H J. Triple-Layer Appearance of Brodmann Area 4 at Thin-Section Double Inversion-Recovery MR Imaging1. Radiology. 2009; 250:515. [PubMed: 19098226]
92. Kobayashi Y, Amaral D. Macaque monkey retrosplenial cortex: I. Three-dimensional and cytoarchitectonic organization. The Journal of comparative neurology. 2000; 426:339-365. [PubMed: 10992242]
93. Koenig S. Cholesterol of myelin is the determinant of gray white contrast in MRI of brain. Magnetic Resonance in Medicine. 1991; 20:285-291. [PubMed: 1775053]
94. Kolster H, Peeters R, Orban G. The Retinotopic Organization of the Human Middle Temporal Area MT/V5 and Its Cortical Neighbors. Journal of Neuroscience. 2010; 30:9801. [PubMed: 20660263]
95. Koyama M, Hasegawa I, Osada T, Adachi Y, Nakahara K, Miyashita Y. Functional Magnetic Resonance Imaging of Macaque Monkeys Performing Visually Guided Saccade Tasks:: Comparison of Cortical Eye Fields with Humans. Neuron. 2004; 41:795-807. [PubMed: 15003178]
96. Krubitzer L, Clarey J, Tweedale R, Elston G, Calford M. A redefinition of somatosensory areas in the lateral sulcus of macaque monkeys. Journal of Neuroscience. 1995; 15:3821. [PubMed: 7751949]
97. Krubitzer L A, Kaas J H. The organization and connections of somatosensory cortex in marmosets. Journal of Neuroscience. 1990; 10:952. [PubMed: 2108231]
98. Kurth F, Eickhoff S, Schleicher A, Hoemke L, Zilles K, Amunts K. Cytoarchitecture and probabilistic maps of the human posterior insular cortex. Cerebral Cortex. 2009
99. Lewis J, Van Essen D. Corticocortical connections of visual, sensorimotor, and multimodal processing areas in the parietal lobe of the macaque monkey. The Journal of comparative neurology. 2000; 428:112-137. [PubMed: 11058227]
100. Lobel E, Kahane P, Leonards U, Grosbras M H, Lehéricy S, Le Bihan D, Berthoz A. Localization of human frontal eye fields: anatomical and functional findings of functional magnetic resonance imaging and intracerebral electrical stimulation. Journal of Neurosurgery: Pediatrics. 2001:95.
101. Mai, J.; Assheuer, J.; Paxinos, G. Atlas of the human brain: Academic Pr. 1997.
102. Malikovic A, Amunts K, Schleicher A, Mohlberg H, Eickhoff S, Wilms M, Palomero-Gallagher N, Armstrong E, Zilles K. Cytoarchitectonic analysis of the human extrastriate cortex in the region of V5/MT+: a probabilistic, stereotaxic map of area hOc5. Cerebral Cortex. 2007; 17:562. [PubMed: 16603710]
103. Marques J P, Kober T, Krueger G, van der Zwaag W, Van de Moortele P F, Gruetter R. MP2RAGE, a self bias-field corrected sequence for improved segmentation and T1-mapping at high field. Neuroimage. 2010; 49:1271-1281. [PubMed: 19819338]
104. Matelli M, Luppino G, Rizzolatti G. Architecture of superior and mesial area 6 and the adjacent cingulate cortex in the macaque monkey. The Journal of comparative neurology. 1991; 311:445-462. [PubMed: 1757597]
105. Mesulam M M, Mufson E J. Insula of the old world monkey. Architectonics in the insulo-orbito-temporal component of the paralimbic brain. The Journal of comparative neurology. 1982; 212:1-22. [PubMed: 7174905]
106. Miot-Noirault E, Barantin L, Akoka S, Le Pape A. T2 relaxation time as a marker of brain myelination: experimental MR study in two neonatal animal models. Journal of neuroscience methods. 1997; 72:5-14. [PubMed: 9128162]
107. Morosan P, Rademacher J, Schleicher A, Amunts K, Schormann T, Zilles K. Human primary auditory cortex: cytoarchitectonic subdivisions and mapping into a spatial reference system. Neuroimage. 2001; 13:684-701. [PubMed: 11305897]
108. Morris R, Paxinos G, Petrides M. Architectonic analysis of the human retrosplenial cortex. The Journal of comparative neurology. 2000; 421:14-28. [PubMed: 10813770]
109. Nelson S M, Cohen A L, Power J D, Wig G S, Miezin F M, Wheeler M E, Velanova K, Donaldson D I, Phillips J S, Schlaggar B L, Petersen S E. A parcellation scheme for human left lateral parietal cortex. Neuron. 2010; 67:156-170. [PubMed: 20624599]
110. Öngür D, Ferry A, Price J. Architectonic subdivision of the human orbital and medial prefrontal cortex. The Journal of comparative neurology. 2003; 460:425-449. [PubMed: 12692859]
111. Orban G, Claeys K, Nelissen K, Smans R, Sunaert S, Todd J, Wardak C, Durand J, Vanduffel W. Mapping the parietal cortex of human and non-human primates. Neuropsychologia. 2006; 44:2647-2667. [PubMed: 16343560]
112. Palomero Gallagher N, Mohlberg H, Zilles K, Vogt B. Cytology and receptor architecture of human anterior cingulate cortex. The Journal of comparative neurology. 2008; 508:906-926. [PubMed: 18404667]
113. Palomero Gallagher N, Vogt B, Schleicher A, Mayberg H, Zilles K. Receptor architecture of human cingulate cortex: Evaluation of the four region neurobiological model. Human brain mapping. 2009; 30:2336-2355. [PubMed: 19034899]
114. Pandya D N, Sanides F. Architectonic parcellation of the temporal operculum in rhesus monkey and its projection pattern. Anatomy and Embryology. 1973; 139:127-161.
115. Paus T. Primate anterior cingulate cortex: where motor control, drive and cognition interface. Nature Reviews Neuroscience. 2001; 2:417-424.
116. Petrides M, Pandya D. Dorsolateral prefrontal cortex: comparative cytoarchitectonic analysis in the human and the macaque brain and corticocortical connection patterns. European Journal of Neuroscience. 1999; 11:1011-1036. [PubMed: 10103094]
117. Pitzalis S, Galletti C, Huang R, Patria F, Committeri G, Galati G, Fattori P, Sereno M. Wide-field retinotopy defines human cortical visual area V6. Journal of Neuroscience. 2006; 26:7962. [PubMed: 16870741]
118. Preuss T M, Goldman Rakic P S. Myelo and cytoarchitecture of the granular frontal cortex and surrounding regions in the strepsirhine primate Galago and the anthropoid primate Macaca. The Journal of comparative neurology. 1991; 310:429-474. [PubMed: 1939732]
119. Preuss T M, Stepniewska I, Kaas J H. Movement representation in the dorsal and ventral premotor areas of owl monkeys: a microstimulation study. The Journal of comparative neurology. 1996; 371:649-676. [PubMed: 8841916]
120. Rademacher J, Caviness V Jr, Steinmetz H, Galaburda A. Topographical variation of the human primary cortices: implications for neuroimaging, brain mapping, and neurobiology. Cerebral Cortex. 1993; 3:313. [PubMed: 8400809]
121. Rilling J, Glasser M, Preuss T, Ma X, Zhao T, Hu X, Behrens T. The evolution of the arcuate fasciculus revealed with comparative DTI. Nature neuroscience. 2008; 11:426-428.
122. Rizzolatti G, Luppino G, Matelli M. The classic supplementary motor area is formed by two independent areas. Advances in neurology. 1996; 70:45-56. [PubMed: 8615224]
123. Rottschy C, Eickhoff S, Schleicher A, Mohlberg H, Kujovic M, Zilles K, Amunts K. Ventral visual cortex in humans: Cytoarchitectonic mapping of two extrastriate areas. Human brain mapping. 2007; 28:1045-1059. [PubMed: 17266106]
124. Salat D, Lee S, van der Kouwe A, Greve D, Fischl B, Rosas H. Age-associated alterations in cortical gray and white matter signal intensity and gray to white matter contrast. Neuroimage. 2009; 48:21-28. [PubMed: 19580876]
125. Scheperjans F, Hermann K, Eickhoff S, Amunts K, Schleicher A, Zilles K. Observer-independent cytoarchitectonic mapping of the human superior parietal cortex. Cerebral Cortex. 2008a; 18:846. [PubMed: 17644831]
126. Scheperjans F, Eickhoff S, Homke L, Mohlberg H, Hermann K, Amunts K, Zilles K. Probabilistic maps, morphometry, and variability of cytoarchitectonic areas in the human superior parietal cortex. Cerebral Cortex. 2008b
127. Ségonne F, Dale A, Busa E, Glessner M, Salat D, Hahn H, Fischl B. A hybrid approach to the skull stripping problem in MRI. Neuroimage. 2004; 22:1060-1075. [PubMed: 15219578]
128. Sereno M, Pitzalis S, Martinez A. Mapping of contralateral space in retinotopic coordinates by a parietal cortical area in humans. Science. 2001; 294:1350. [PubMed: 11701930]

129. Shulman G, McAvoy M, Cowan M, Astafiev S, Tansy A, d'Avossa G, Corbetta M. Quantitative analysis of attention and detection signals during visual search. Journal of Neurophysiology. 2003; 90:3384. [PubMed: 12917383]
130. Sled J, Zijdenbos A, Evans A. A nonparametric method for automatic correction of intensity nonuniformity in MRI data. Medical Imaging, IEEE Transactions on. 2002; 17:87-97.
131. Sled J G, Zijdenbos A P, Evans A C. A nonparametric method for automatic correction of intensity nonuniformity in MRI data. Medical Imaging, IEEE Transactions on. 1998; 17:87-97.
132. Stanton G, Deng S Y, Goldberg E, McMullen N. Cytoarchitectural characteristic of the frontal eye fields in macaque monkeys. The Journal of comparative neurology. 1989; 282:415-427. [PubMed: 2715390]
133. Steen R, Reddick W, Ogg R. More than meets the eye: significant regional heterogeneity in human cortical T1. Magnetic resonance imaging. 2000; 18:361-368. [PubMed: 10788712]
134. Swisher J, Halko M, Merabet L, McMains S, Somers D. Visual topography of human intraparietal sulcus. Journal of Neuroscience. 2007; 27:5326. [PubMed: 17507555]
135. Tootell R B H, Taylor J B. Anatomical evidence for M T and additional cortical visual areas in humans. Cerebral Cortex. 1995; 5:39. [PubMed: 7719129]
136. Triarhou L. The Economo-Koskinas Atlas revisited: cytoarchitectonics and functional context. Stereotactic and Functional Neurosurgery. 2007a; 85:195-203. [PubMed: 17534132]
137. Triarhou L. A proposed number system for the 107 cortical areas of Economo and Koskinas, and Brodmann area correlations. Stereotactic and Functional Neurosurgery. 2007b; 85:204-215. [PubMed: 17534133]
138. Van de Moortele P, Auerbach E, Olman C, Yacoub E, Ugurbil K, Moeller S. T1 weighted brain images at 7 Tesla unbiased for Proton Density, T2 contrast and RF coil receive B1 sensitivity with simultaneous vessel visualization. Neuroimage. 2009; 46:432-446. [PubMed: 19233292]
139. Van Essen D, Drury H, Dickson J, Harwell J, Hanlon D, Anderson C. An integrated software suite for surface-based analyses of cerebral cortex. Journal of the American Medical Informatics Association. 2001; 8:443. [PubMed: 11522765]
140. Van Essen D C, Dierker D L. Surface-based and probabilistic atlases of primate cerebral cortex. Neuron. 2007; 56:209-225. [PubMed: 17964241]
141. Vogt B, Vogt L. Cytology of human dorsal midcingulate and supplementary motor cortices. Journal of Chemical Neuroanatomy. 2003; 26:301-309. [PubMed: 14729132]
142. Vogt, B.; Hof, P.; Vogt, L. Cingulate gyrus. In: Paxinos, G.; Mai, J., editors. The Human Nervous System. Elsevier; Amsterdam: 2004. p. 915-949.
143. Vogt B, Vogt L, Laureys S. Cytology and functionally correlated circuits of human posterior cingulate areas. Neuroimage. 2006; 29:452-466. [PubMed: 16140550]
144. Vogt B, Nimchinsky E, Vogt L, Hof P. Human cingulate cortex: surface features, flat maps, and cytoarchitecture. The Journal of comparative neurology. 1995; 359:490-506. [PubMed: 7499543]
145. Vogt B A, Vogt L, Farber N B, Bush G. Architecture and neurocytology of monkey cingulate gyrus. The Journal of comparative neurology. 2005; 485:218. [PubMed: 15791645]
146. Vorobiev V, Govoni P, Rizzolatti G, Matelli M, Luppino G. Parcellation of human mesial area 6: cytoarchitectonic evidence for three separate areas. European Journal of Neuroscience. 1998; 10:2199-2203. [PubMed: 9753106]
147. Wallace M N, Johnston P W, Palmer A R. Histochemical identification of cortical areas in the auditory region of the human brain. Experimental Brain Research. 2002; 143:499-508.
148. Walters N, Egan G, Kril J, Kean M, Waley P, Jenkinson M, Watson J. In vivo identification of human cortical areas using high-resolution MRI: an approach to cerebral structure-function correlation. Proceedings of the National Academy of Sciences of the United States of America. 2003; 100:2981. [PubMed: 12601170]
149. Walters N, Eickhoff S, Schleicher A, Zilles K, Amunts K, Egan G, Watson J. Observer-independent analysis of high-resolution MR images of the human cerebral cortex: in vivo delineation of cortical areas. Human brain mapping. 2007; 28:1-8. [PubMed: 16773636]
150. Wilms M, Eickhoff S B, Specht K, Amunts K, Shah N J, Malikovic A, Fink G R. Human V5/MT+: comparison of functional and cytoarchitectonic data. Anatomy and Embryology. 2005; 210:485-495. [PubMed: 16328357]
151. Yoshiura T, Higano S, Rubio A, Shrier D, Kwok W, Iwanaga S, Numaguchi Y. Heschl and Superior Temporal Gyri: Low Signal Intensity of the Cortex on T2-weighted MR Images of the Normal Brain1. Radiology. 2000; 214:217. [PubMed: 10644127]
152. Zhang Y, Brady M, Smith S. Segmentation of brain MR images through a hidden Markov random field model and the expectation-maximization algorithm. Medical Imaging, IEEE Transactions on. 2002; 20:45-57.
153. Zilles, K. Regional and laminar organization. The human nervous system Amsterdam: Elsevier Academic Press; 2004. Architecture of the human cerebral cortex; p. 997-1055.
154. Zilles K, Amunts K. Centenary of Brodmann's map-conception and fate. Nature Reviews Neuroscience. 2010; 11:139-145.

What is claimed is:

1. A method of classifying myelin components to determine whether a biological structure of the nervous system contains myelin, the method comprising, at a system having a memory and one or more processor for processing and displaying images of the biological structure: computationally processing at least a T1 weighted magnetic resonance image of the structure and a T2 weighted magnetic resonance image of the structure in order to analyze at least a portion of the structure of the nervous system using a plurality of stored tissue classifier elements developed using statistical modeling to determine if the portion of the structure correlates with the presence of myelin, in which event the portion of the structure is determined to contain myelin, wherein the computational processing includes:

registering the T2 weighted magnetic resonance image with the T1 weighted magnetic resonance image by aligning a voxel in the T2 weighted magnetic resonance image with a corresponding voxel in the T1 weighted magnetic resonance image; and dividing, for each voxel in the registered T2 weighted image, a first intensity value in the registered T2 weighted image by a second intensity value of the corresponding voxel in the T1 weighted magnetic resonance image to generate a map of the biological structure.

2. The method of claim 1, wherein said computation processing further includes scaling the map of the biological structure by a constant value.

3. The method of claim 1, wherein the plurality of stored tissue classifier elements are developed using reference data by multivariate regression.

4. The method of claim 1, wherein the plurality of stored tissue classifier elements is determined by a process selected from the group consisting of post-operative histological examination, direct tissue inspection, and labeling by one or more experts.

5. The method of claim 1, wherein the biological structure is the brain or spinal cord.

6. The method of claim 1, wherein the computation processing further includes applying a mask to identify a specific tissue type in the biological structure.

7. The method of claim 6, wherein the specific tissue type is white matter.

8. The method of claim 6, wherein the specific tissue type is gray matter.

9. The method of claim 1, wherein the computation processing further includes generating a Z-score map by comparing the map of the biological structure to a reference map.

10. The method of claim 9, wherein the reference map is generated from data of biological structure from a normal subject or a subject having a disease.

11. The method of claim 1, wherein the biological structure is of the central nervous system.

12. The method of claim 1, wherein the computation processing further includes applying a mask to suppress noise.

13. The method of claim 1, further comprising communicating results of the computational processing and determination of whether the biological structure contains myelin to a remote address.

14. A method of assessing effectiveness of a therapeutic regimen, comprising:
   a) determining a myelin volume in at least a portion of a biological structure of a patient using the method of claim 1;
   b) delivering to the patient a therapeutic regimen comprising administration of a drug expected to stabilize or increase myelin volume over the course of the therapeutic regimen; and
   c) during and/or at the end of the therapeutic regimen, determining whether the myelin volume has stabilized or been increased, thereby allowing assessment of the effectiveness of the therapeutic regimen.

* * * * *